(12) United States Patent
Schnall

(10) Patent No.: US 7,819,811 B2
(45) Date of Patent: Oct. 26, 2010

(54) DETECTING MEDICAL CONDITIONS WITH NONINVASIVE BODY PROBES

(75) Inventor: Robert P. Schnall, Kiryat Bialik (IL)

(73) Assignee: Itamar Medical Ltd., Caesarea (IL)

( * ) Notice: Subject to any disclaimer, the term of this patent is extended or adjusted under 35 U.S.C. 154(b) by 1365 days.

(21) Appl. No.: 10/533,970

(22) PCT Filed: Nov. 6, 2003

(86) PCT No.: PCT/IL03/00930

§ 371 (c)(1),
(2), (4) Date: May 4, 2005

(87) PCT Pub. No.: WO2004/041079

PCT Pub. Date: May 21, 2004

(65) Prior Publication Data

US 2006/0104824 A1 May 18, 2006

Related U.S. Application Data

(60) Provisional application No. 60/423,974, filed on Nov. 6, 2002.

(51) Int. Cl.
*A61B 5/00* (2006.01)
(52) U.S. Cl. .................. 600/500; 600/504; 600/309
(58) Field of Classification Search .................. None
See application file for complete search history.

(56) References Cited

U.S. PATENT DOCUMENTS

| | | | |
|---|---|---|---|
| 4,331,154 A * | 5/1982 | Broadwater et al. | 600/490 |
| 5,111,817 A | 5/1992 | Clark et al. | |
| 5,140,990 A | 8/1992 | Jones et al. | |
| 5,188,108 A * | 2/1993 | Secker | 600/310 |
| 5,566,677 A | 10/1996 | Raines et al. | |
| 6,319,205 B1 * | 11/2001 | Goor et al. | 600/485 |
| 6,322,515 B1 | 11/2001 | Goor et al. | |
| 6,375,620 B1 * | 4/2002 | Oser et al. | 600/481 |

(Continued)

OTHER PUBLICATIONS

Communication Pursuant to Article 94(3) EPC Dated Apr. 21, 2010 From the European Patent Office Re.: Application No. 03810573.0.

(Continued)

*Primary Examiner*—Robert L Nasser

(57) ABSTRACT

A method and apparatus for improving the diagnostic performance of a probe system (30) for detecting a medical condition in a patient by sensing volume changes in a monitored body part due to pulsatile arterial blood flow in the body part, characterized in calibrating the probe system (30) for the respective measurement site according to a predetermined characteristic of the monitored body part of the patient and quantifying the arterial pulsatile volume thereat. Such calibration is described with respect to probes including: (1) a pressure sensor (63), which senses pressure changes in a compressible fluid system to which the patient's body part (e.g., finger, toe or a distal portion of a limb) is subjected, which pressure changes are convertible to volume changes in the body part due to pulsatile arterial blood volume changes therein; and (2) an optical sensor (140), which senses optical density or transmissivity changes in the body part, which changes are also convertible to volume changes due to pulsatile arterial blood volume changes in the body part.

36 Claims, 15 Drawing Sheets

U.S. PATENT DOCUMENTS 6,461,305 B1 10/2002 Schnall
6,488,633 B1 12/2002 Schnall
2003/0050541 A1* 3/2003 Wuori ..................... 600/316

OTHER PUBLICATIONS

Supplementary European Search Report Dated Feb. 1, 2010 From the European Patent Office Re.: Application No. 03810573.0.

* cited by examiner

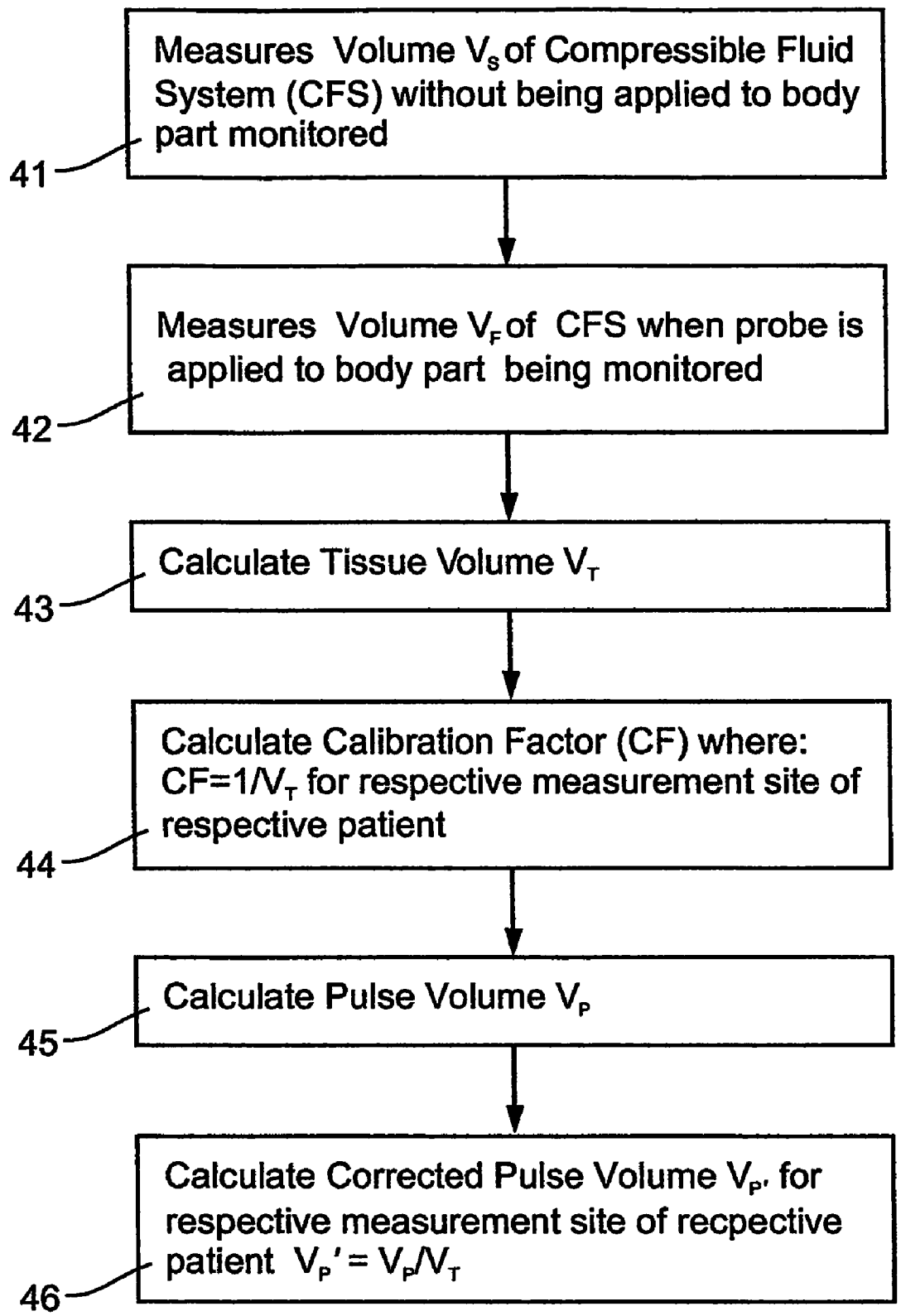
Fig. 2 (Overall Flow Chart)

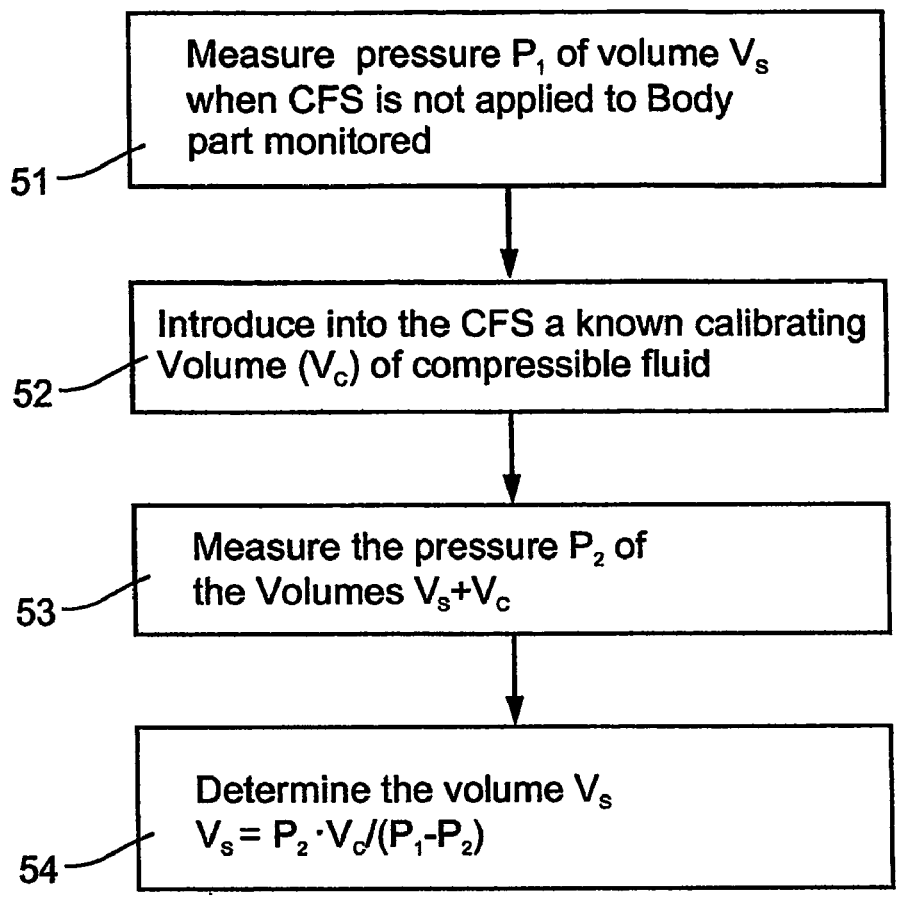
Fig. 3 (Determine Volume $V_s$)
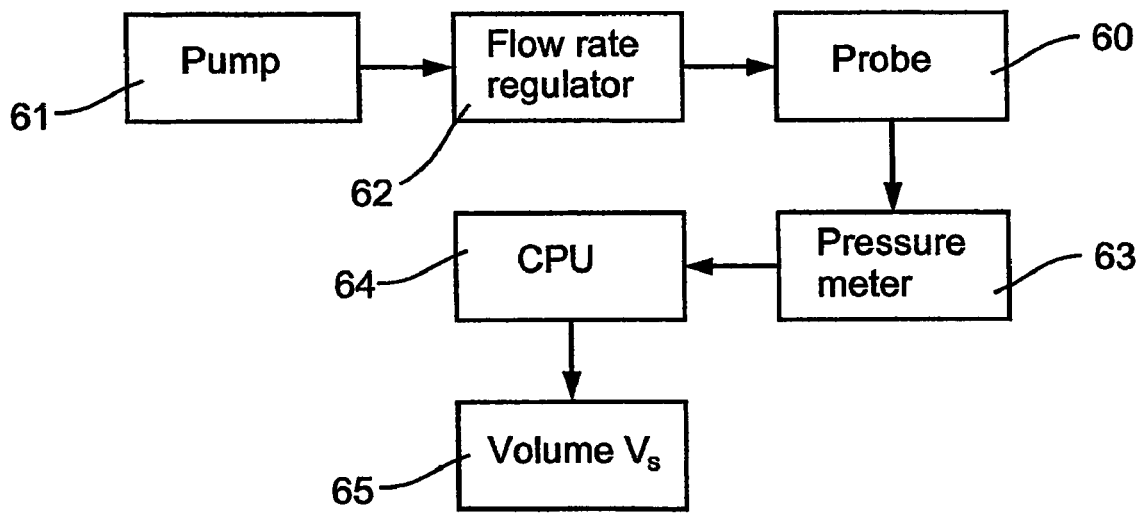
Fig. 4

Fig. 5 (Determine Volume $V_s$)

Fig. 6 (Determine Tissue Volume $V_T$)

Fig. 7 (Calculate $V_P$ and $V_P'$)

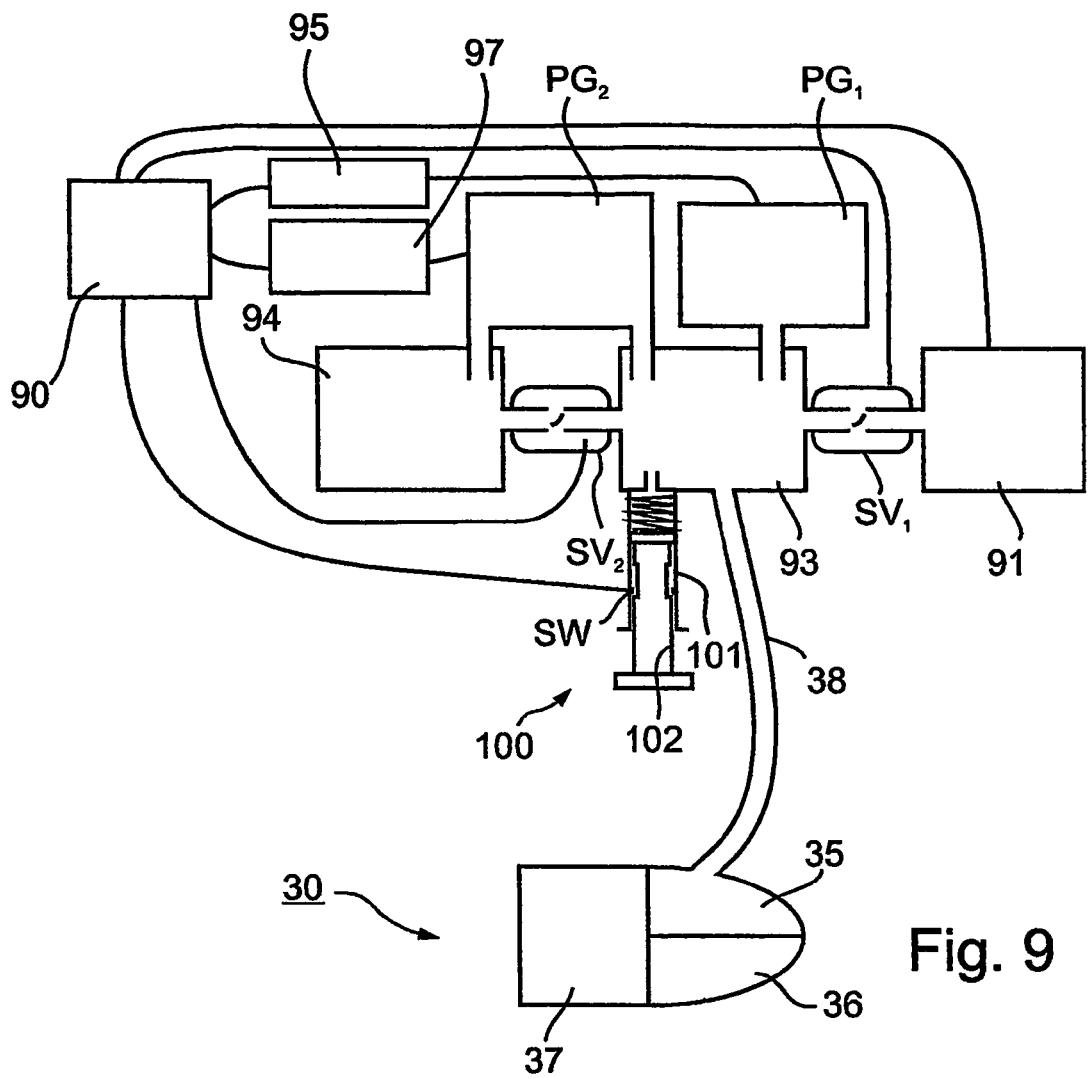
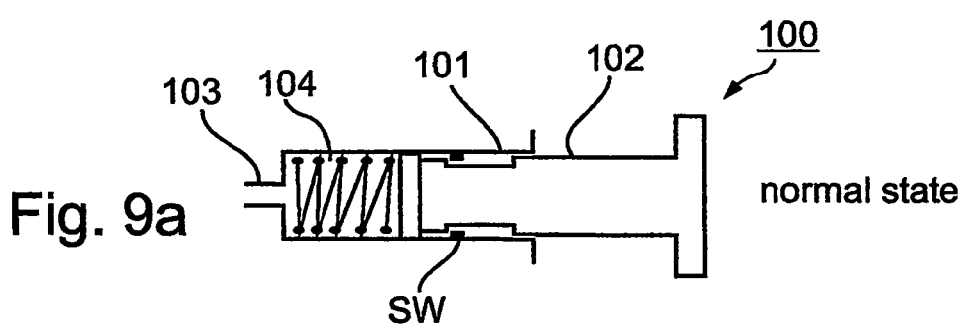
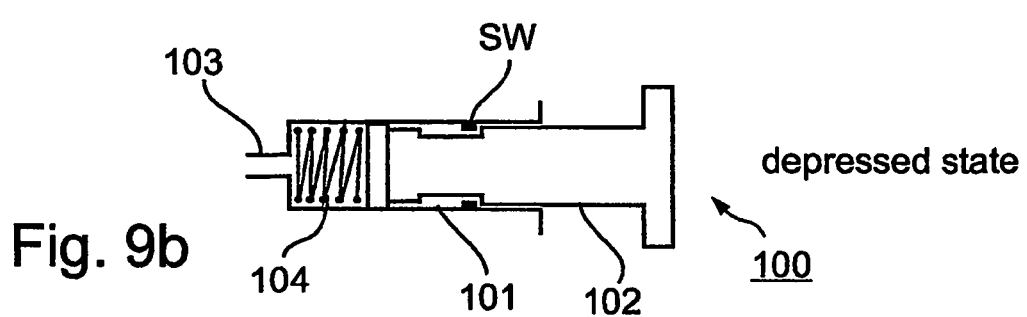

DETECTING MEDICAL CONDITIONS WITH NONINVASIVE BODY PROBES

RELATED PATENT APPLICATION

This application is a National Phase Application of PCT/IL03/00930 having International Filing Date of 6 Nov. 2003, which claims benefit of U.S. Provisional Patent Application No. 60/423,974 filed 6 Nov. 2002.

FIELD AND BACKGROUND OF THE INVENTION

The present invention relates to a method and apparatus for using body probes in the non-invasive detection of medical conditions. The invention is particularly useful with respect to the probes described in U.S. Pat. Nos. 6,319,205, 6,322,515, 6,461,305 and 6,488,633, and in International Patent Applications PCT/IL02/00249 and PCT/IL03/00586, the contents of which are incorporated herein by reference, and is therefore described below especially with respect to such probes.

The above U.S. Patents and International Patent Application describe non-invasive methods of detecting various medical conditions in a patient by using probes to monitor volume changes in a body part due to pulsatile arterial blood flow in the body part. The probes described in the above four U.S. patents were constructed generally for application to a finger or toe of the patient for monitoring changes in the peripheral arterial tone thereat. The above International Applications describe other probes constructed for application to other selected areas of the patient particularly for monitoring the peripheral arterial tone thereat. The various medical conditions detected by such probes include mycardial ischemia, sleep apnea and other sleep disordered breathing conditions and sleep disorders, endothelial dysfunction (ED), as well as certain physiological states, such as mental stress, sympathetic nervous system reactivity, blood pressure, REM stage sleep, and responses to physical or pharmacological agents.

Among the various types of probes described were those including: (1) pressure sensors, which sense pressure changes in a compressible fluid system to which the patient's body part (e.g., finger, toe or a distal portion of a limb) is subjected, which pressure changes are convertible to volume changes in the body part due to pulsatile arterial blood volume changes therein; and (2) optical sensors, which sense optical density or transmissivity changes in the body part, which changes are also convertible to volume changes due to pulsatile arterial blood volume changes in the body part.

Such probes generally did not require accurate calibration for the respective measurement site of the respective patient since the measurements were only of relative changes in volume to be compared with the patient's own base line results observed during the tests. The determination of such relative volume changes over time provided clinically useful information regarding the various medical conditions of the patient as described in the above U.S. Patents and International Applications.

OBJECT AND BRIEF SUMMARY OF THE PRESENT INVENTION

A main object of the present invention is to provide a method and apparatus enabling probes generally, and more particularly the probes described in the above-cited U.S. Patents and International Patent Applications, to be more effectively used in the non-invasive determination of medical conditions.

According to one aspect of the present invention, there is provided a method of improving the diagnostic performance of a probe system for detecting a medical condition in a patient, which probe system includes at least one probe for sensing volume or volume-related changes in a monitored body part due to pulsatile arterial blood flow in the body part, characterized in calibrating the probe system for the respective measurement site of the respective patient according to predetermined characteristics of the monitored body part of the patient and quantifying the arterial pulsatile volume thereat.

The present invention is thus based on the dual features that: 1) calibrating the probe for certain physical characteristics, e.g., the tissue volume of the monitored body part (e.g., finger, toe or a distal portion of a limb) of the respective patient can improve the diagnostic performance of the probe and the reproducibility of the measurements; and 2) accurately quantifying the magnitude of arterial pulsatile volume changes can likewise improve the diagnostic performance of the probe and the reproducibility of the measurements.

Although in International Application PCT/IL01/00970 relating to Method and Apparatus for Non-Invasively Evaluating Endothelial Activity in a Patient, some described preferred embodiments utilized the measured baseline amplitude of the measured peripheral arterial pulsatile flow itself to adjust the response to blood flow occlusion, there was no particular description of any specific means for quantitatively determining the baseline amplitude, nor any discussion of measuring the volume of the tissue from which signals were derived, or of otherwise calibrating the probe system for the respective measurement site of the respective patient according to predetermined characteristics of the monitored body part of the patient.

The manner in which the above dual features are accomplished is described below particularly with the aid of the diagram of FIG. 1a, wherein:

$V_S$=the total volume of a compressible fluid system when not applied to the monitored body part;

$V_F$=volume of the compressible fluid in the compressible fluid system when applied to the monitored body part;

$V_T$=tissue volume (i.e., incompressable body part volume) contained within $V_S$, i.e., $V_T=V_S-V_F$;

$V_C$=a known calibrating volume;

$V_P$=pulsitatively-variable volume corresponding to arterial volume changes;

$V_{min}$=minimum volume of pulsatile component of tissue volume (corresponds to $V_T$); and $V_{max}$=maximum volume of pulsatile component of tissue volume;

For example, in probes utilizing pressure sensors which sense pressure changes in a compressible fluid system, the volume/pressure relationship which enables the sensed pressure to be converted to volume changes is applicable only with respect to the compressible fluid in such a system, and not to the non-compressible tissue of the body part to which the compressible fluid system is applied when making the pressure measurements. That is, the effective volume of the compressible fluid system is effectively reduced by the volume of the tissue in the body part in which the pulsatile arterial blood flow is monitored. Thus, knowledge of the actual volume of the non-compressible tissue ($V_T$, FIG. 1a) of the body part, and of the residual effective compressible fluid ($V_F$) within the overall compressible fluid system ($V_S$), enables the sensed pulsatile pressure measurements to be more accurately translated to the actual pulsatile volume changes, and thereby provides a more accurate indication of the subject's medical condition.

In addition, calibrating the probe for the respective patient better enables establishing a base line for the subsequent evaluation of the patient's response to a prescribed procedure. It thereby provides a better indication of any changes in the patient's medical condition and facilitates comparisons between tests performed at different times. This is particularly true in testing the response of the patient to exercise stress or to a prescribed period of blood flow occlusion in testing the patient's endothelial function. In the latter cases, the absolute pulse magnitude as well as the relative pulse changes preferably normalized to the size of the tissue examined, are important in evaluating the response to the stimulus.

Further, since the gain of the measuring system is substantially affected by the relationship of the tissue volume ($V_T$) of the body part to the volume of the compressible fluid in the overall system ($V_S$), a change in the tissue volume $V_T$ produces a corresponding change in the sensed parameter (e.g., pressure swings in probes using a pressure sensor) accompanying a pulsatile volume change due to pulsatile arterial blood flow in the respective body part (e.g., finger, toe or a distal portion of a limb). By thus, predetermining the relative volumes $V_T$ and $V_F$ in the volume $V_S$ of the compressible fluid system, particularly when verifying such determinations as will be described more particularly below, a substantial improvement is attainable in the diagnostic performance, and in the reproducibility, of the measurements when using such probes for non-invasively monitoring medical conditions.

A further important feature that the calibration of the probe can provide is that it may facilitate the accurate measurement of the magnitude of the pulsatile volume changes accompanying arterial pulse-waves by expressing them with respect to the tissue volume from which they are derived, thereby yielding a value of pulsatile volume per unit of tissue mass. This may facilitate the comparison of values between studies by providing a universal index of pulsatile volume normalized to the volume of tissue from which they are measured.

The invention is described more particularly below with respect to two types of probes (pressure-sensor and optical-sensor types) for sensing volume changes in a body part (e.g., finger, toe or a distal portion of a limb) due to pulsatile arterial blood flow therein.

In one group of embodiments, the probe includes a pressure sensor which senses the volume changes by sensing changes in pressure in a compressible fluid system applied to the body part; The body part includes a fixed volume of non-compressible tissue ($V_T$) and a pulsitatively variable volume ($V_P$) such that the pressure in the compressible fluid system changes with the change in pulsatile volume thereof, and the gain of such changes varies according to the relationship of the volumes $V_T$ and $V_F$.

The latter relationship is preferably determined by: determining the volume $V_S$ of the compressible fluid system when not applied to the monitored body part; determining the volume $V_F$ of the compressible fluid system when applied to the monitored body part; and subtracting $V_F$ from $V_S$ to produce the volume $V_T$ of the non-compressible tissue.

In other embodiments described below, the probe includes an optical sensor having a light source and a light receiver. The probe is calibrated for the respective patient by the use of a model which modifies the light source to produce in the light receiver a waveform simulating that produced by the pulsatile arterial blood flow in the body part of the respective patient.

For example, in one described preferred embodiment, the model includes a light-transmissive body illuminated by the light source, and a function generator for generating a waveform to drive the light source such as to produce in the light receiver a waveform simulating that produced by the pulsatile arterial blood flow in the body part of the respective patient to thereby quantify the arterial pulsatile volume thereat.

In another described preferred embodiment, the model includes a porous light-transmissive matrix simulating the vascular bed of the non-compressible tissue in the body part of the respective patient; a liquid light-absorbing medium; and a pump for pumping the liquid light-absorbing medium through the porous matrix in a manner analogous to the pulsatile arterial blood flow through the body part of the respective patient to thereby facilitate the quantification of the arterial pulse volume thereat.

In all the embodiments of the invention described below, the body part is a finger, toe or distal portion of a limb of the patient, and the probe encloses the body part such as to monitor the peripheral arterial tone thereof. However, it will be appreciated that the body part to which the probe is applied could be another selected area of the subject's skin, such as one occupying a relatively small fraction of the surface perimeter of the respective body part at the measurement site, to thereby permit free venous drainage from the measurement site via a wide region of unrestricted passageways surrounding the measurement site, as described in the above-cited International Patent Application PCT/IL03/00586.

According to another aspect of the present invention, there is also provided apparatus for detecting a medical condition of a patient, comprising: a probe system including a probe to be applied to a measurement site of the patient for sensing volume or volume-related changes in a monitored body part thereat due to pulsatile arterial blood flow in the body part; and calibrating means for calibrating the probe system for the respective measurement site, according to a predetermined physical characteristic of the body part of the respective patient and for quantifying the arterial pulse volume thereat.

In preferred embodiments of the invention described below, the predetermined characteristic of the monitored body part for which the probe system is calibrated includes the relative volume of the tissue therein.

According to further features in one described preferred embodiment the probe includes a pressure sensor which senses the volume changes by sensing changes in pressure in a compressible fluid system of volume $V_F$ when applied to the monitored body part and of volume $V_S$ where not applied to the body part, the body part including a fixed volume $V_T$ of non-compressible tissue and a pulsitatively-variable volume $V_P$ corresponding to arterial volume changes, such that the pressure in the compressible fluid system changes with the change in pulsatile volume thereof and the gain of the changes varies according to the relative values of the volumes $V_T$ and $V_F$. The calibrating means includes a data processor programmed to determine the volume $V_S$ of the compressible fluid system according to the following equation:

$$V_S = P_2 \cdot V_C / (P_1 - P_2) \quad \text{(Eq. 1)}$$

wherein:

$P_1$ is the pressure of the compressible fluid system, of volume $V_F$, when not applied to the monitored body part; $V_C$ is the volume of a known calibrating volume of compressible fluid added to the compressible fluid system after measuring pressure $P_1$; and $P_2$ is the pressure of the compressible fluid system after the volume $V_C$ of calibrating fluid has been added thereto.

According to further features in that described preferred embodiment, the data processor is programmed to determine the volume $V_T$ of the non-compressible tissue according to the following equations:

$$V_F = P_2 \cdot V_C / (P_1 - P_2) \quad \text{(Eq. 2)}$$

$$V_T = V_S - V_F \quad \text{(Eq. 3)}$$

As will be described more particularly below, calibrating the probe system for the respective measurement site of the respective patient as described above enables any pressure fluctuations in the system accompanying pulse waves to be subsequently accurately converted into volume changes using Boyles Law. Furthermore, the pulsatile volume changes may be expressed as a fraction of the size of the tissue being measured so as to yield a universal index of pulsatile volume normalized to the volume of tissue from which they are measured. As a corollary to the indirect determination of volume changes based on measuring pressure changes within the system and the appropriate application of Boyles Law as described above, it will also be apparent that the measurement of volume changes could also be determined by generating pulsatile volume changes of known volume which match the observed pressure changes.

In other described preferred embodiments, the probe system includes an optical sensor having a light source and a light receiver; and the probe system is calibrated for the respective patient by the use of a model which modifies the light source to produce in the light receiver a waveform simulating that produced by the pulsatile arterial blood flow in the body part of the respective patient.

The above method and apparatus are thus capable of substantially improving the diagnostic performance and/or the reproducibility of the measurements when using such probes for the non-invasive detection of various medical conditions.

Further features and advantages of the invention will be apparent from the description below.

BRIEF DESCRIPTION OF THE DRAWINGS

The invention is herein described, by way of example only, with reference to the accompanying drawings, wherein:

FIG. 2 is an overall flow chart illustrating one manner of calibrating the probe of FIG. 1;

FIG. 3 is a flow chart illustrating one manner of performing the first operation in the flow chart of FIG. 2;

FIG. 4 illustrates apparatus for performing the first operation in the flow chart of FIG. 2 in another manner;

FIG. 9 illustrates another form of apparatus for calibrating the probe of FIG. 1;

FIGS. 9a and 9b illustrate the normal and depressed states, respectively, of the manually-operated syringe included in the apparatus of FIG. 9 for introducing the calibrating fluid;

Figure 1:
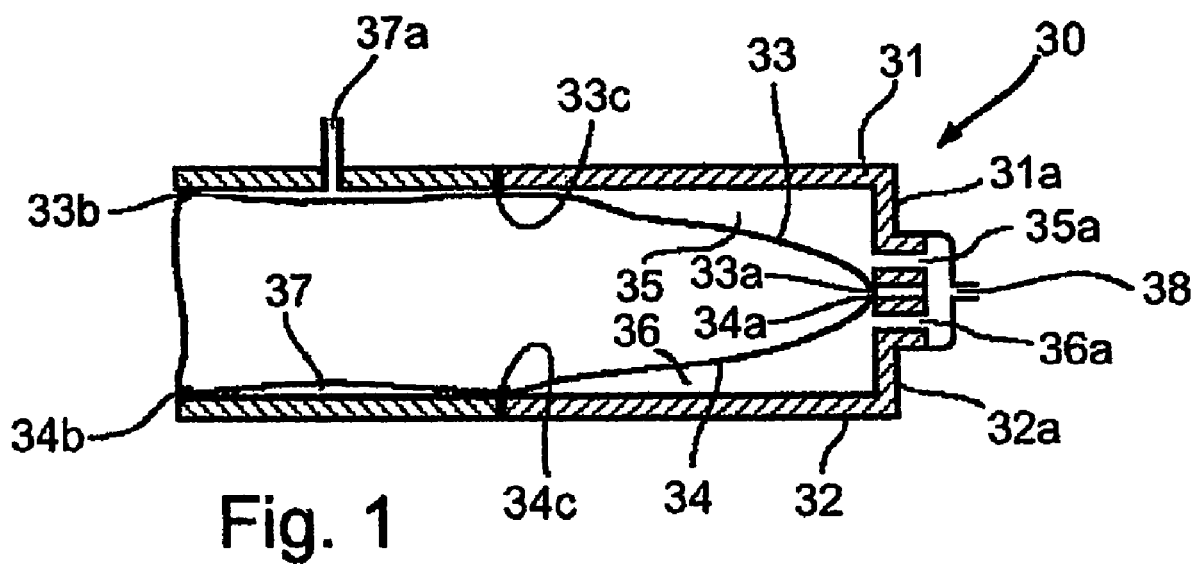
FIG. 1 illustrates one form of probe of the pressure-sensor type which may be calibrated in accordance with the present invention to improve the diagnostic performance and/or reproducibility of measurements when using the probe.

It is to be understood that the foregoing drawings, and the description below, are provided primarily for purposes of facilitating understanding the conceptual aspects of the invention and various possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DETAILED DESCRIPTION

As indicated above, the invention provides a method and apparatus for calibrating probes heretofore used for non-invasively detecting medical conditions in a patient in order to improve the diagnostic performance and/or the reproducibility of the measurements for the respective patient. The invention is particularly useful for probes constructed in accordance with the above-cited U.S. Patents and International Patent Applications for monitoring changes in the peripheral arterial tone of the patient. The invention is therefore described below for purposes of example with respect to the probes described in U.S. Pat. No. 6,319,205. It will be appreciated, however, that the invention, or various features thereof, could also be advantageously used with respect to other types of probes for non-invasively detecting medical conditions, and particularly those described in any of the above-cited U.S. Patents and International Patent Applications.

The preferred embodiments of the invention described in U.S. Pat. No. 6,319,205 detected various medical conditions in a patient by using a probe to monitor the peripheral arterial tone in the patient. This was done by sensing volume changes in a body part of the patient, particularly the patient's finger or toe, due to pulsatile arterial blood volume flow in the body part. Both pressure-sensor and optical-sensor type probes were described. The pressure-sensor type probe sensed the pulsatile volume changes in the body part by sensing pressure changes in a compressible fluid system, which pressure changes were converted to volume changes according to Boyles Law. The optical-sensor type probe sensed the pulsatile volume changes in the body part by sensing optical-density or optical-transmissivity changes in the body part due to the pulsatile arterial blood flow therein, which optical changes were converted to pulsatile volume changes in the body part.

Both types of probes included pressurizing means for applying a static pressure field substantially uniformly to the body part, e.g., to the distal end of the patient's finger including its terminal-most extremity. The pressure field is of a predetermined magnitude sufficient to prevent distention of the venous vasculature, to prevent venous blood pooling within the applied pressure field, and to prevent uncontrolled venous back flow and retrograde shock wave propagation into the distal end of the finger, and also to partially unload the wall tension of, but not occlude, the arteries in the distal end of the finger when at heart level or below. Such a pressure field thus contributes to the optimal measurement of arterial pulse signals divorced from venous volume changes and divorced from confounding induced reflex vascular changes due to artifacts induced by the measurement method.

As indicated above, the measurements made in the above-cited patent were only of relative changes in the monitored body part, since such relative changes, when compared with the patient's own base line results observed during the test, provided clinically useful information regarding various medical conditions of the patient. Therefore, the probes were not accurately calibrated for physical characteristics of the particular patient nor were they configured for quantifying the arterial pulsatile volume in either absolute or relative terms. The present invention is based on the concept that, by calibrating the probes for the respective measurement site of the respective patient for predetermined physical characteristics of the monitored body part, and by quantifying the arterial pulse volume thereat, the diagnostic performance and/or the reproducibility of the measurements can be substantially improved for the respective patient.

Described below are methods and apparatus for calibrating, in accordance with the present invention, both the pressure-sensor type of probe and the optical-sensor type of probe. While the description below refers to the probes described in U.S. Pat. No. 6,319,205, it will be appreciated, as indicated above, that the described method and apparatus are also applicable to the probes described in the other U.S. Patents and in the International Patent Applications cited above.

Calibrating a Pressure-Sensor Type Probe (FIGS. 1-14)

FIG. 1 illustrates a pressure-sensor type probe, generally designated 30, corresponding to the probe illustrated in FIG. 2a of U.S. Pat. No. 6,319,205. The illustrated probe includes a casing constituted of two semi-cylindrical sections 31, 32 defining a tubular socket for receiving the patient's finger. Each section is formed at one end with a partial end wall 31a, 32a and is open at its opposite end. Two membranes 33, 34, are secured: at one edge to one of the end walls 31a, 31b; at the opposite edge to the open end of the respective section, as shown at 33b, 34b, respectively, and at an intermediate portion to the two sections, as shown at 33c and 34c, respectively. The two membranes thus define the two opposing halves of a longitudinally split cylinder or thimble, chambers 35,36 at the distal end of the probe, and a further annular chamber 37 at the proximal end of the probe.

The distal end of the probe is formed with two ports 35a, 36a, communicating with the two chambers 35 and 36; whereas the proximal end of the probe is formed with a port 37a communicating with chamber 37. The two ports 35a, 36a communicate, by means of a connection 38, to a compressible fluid system such that the pulsatile arterial blood flow in the finger received within the probe is sensed as pressure change. Port 37a, communicating with chamber 37, is connected to the fluid system such as to apply a static pressure field substantially uniformly around the respective end of the patient's finger to enable the probe to monitor peripheral arterial tone in the patient's finger.

Further details of the constructions and mode of operation of the probe illustrated in FIG. 1, as well as of the compressible fluid system with which the probe is used for non-invasively detecting various medical conditions of the patient, are described in U.S. Pat. No. 6,319,205, incorporated herein by reference.

Figure 1A:
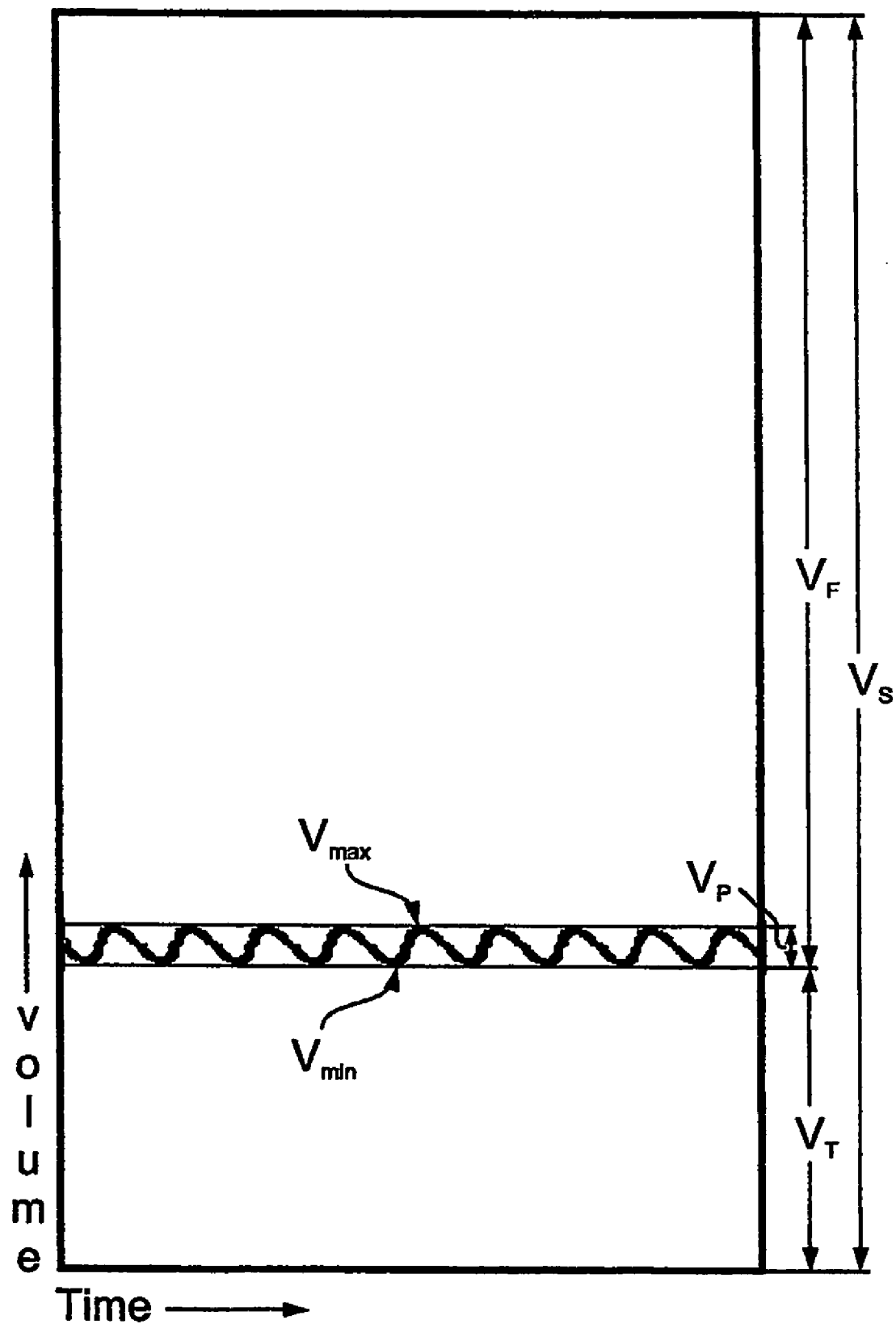
FIG. 1a is a diagram defining, as more particularly described above, the various symbols used in the description below explaining the manner in which the system including the probe of FIG. 1 is calibrated.

While such probes provide clinically useful information as to the medical condition of the patient, it has been found, as briefly described above, that the diagnostic performance of the probe can be substantially improved in many respects by calibrating the probe in accordance with predetermined physical characteristics of the particular body part (e.g., patient's finger) monitored by the probe to detect the medical condition. For example, as shown in FIG. 1a, as the volume of the tissue $V_T$ (substantially non-compressible) in the probe increases, there is a corresponding decrease in the effective residual volume of the compressible fluid in the fluid system sensed by the pressure sensor, and therefore there would be a corresponding increase in the pressure swings sensed by the pressure sensor resulting from a given pulsatile volume change ($V_P$) within the body part. In accordance with one aspect of the present invention, therefore, the magnitude of the volume of the non-compressible tissue ($V_T$), and the effective volume of the compressible fluid system ($V_S$), sensed by the pressure sensor are determined in order to provide pulsatile volume signal calibration of the probe for the given measurement, and thereby to improve the diagnostic capability of the probe system and the ability to compare test results. The value $V_T$ is of further significance in so far as it allows the pulsatile signal value $V_P$ to be standardized to the tissue mass from which it is derived.

Figure 6:
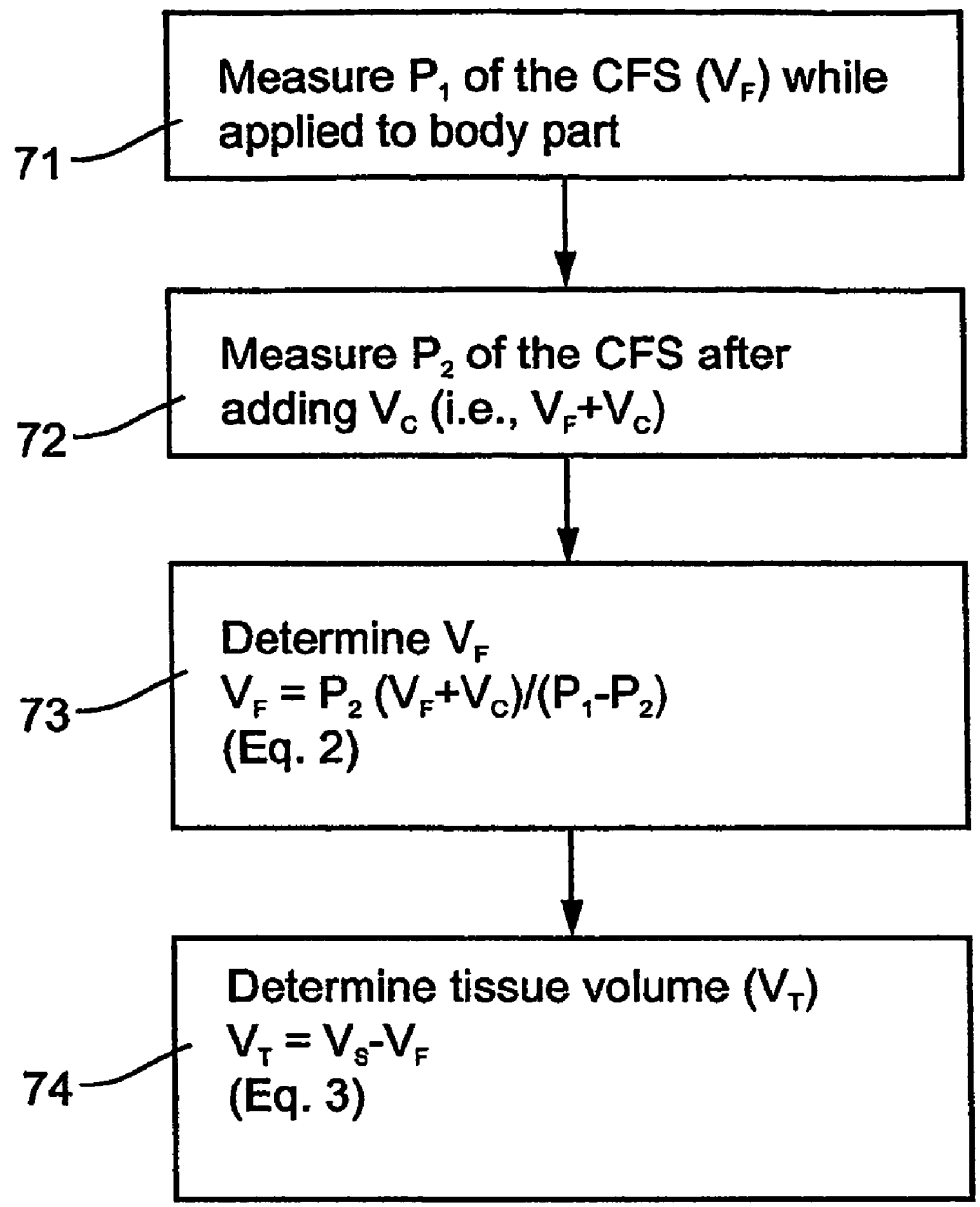
FIG. 6 is a flow chart for performing the second and third operations in the flow chart of FIG. 2.
Figure 7:
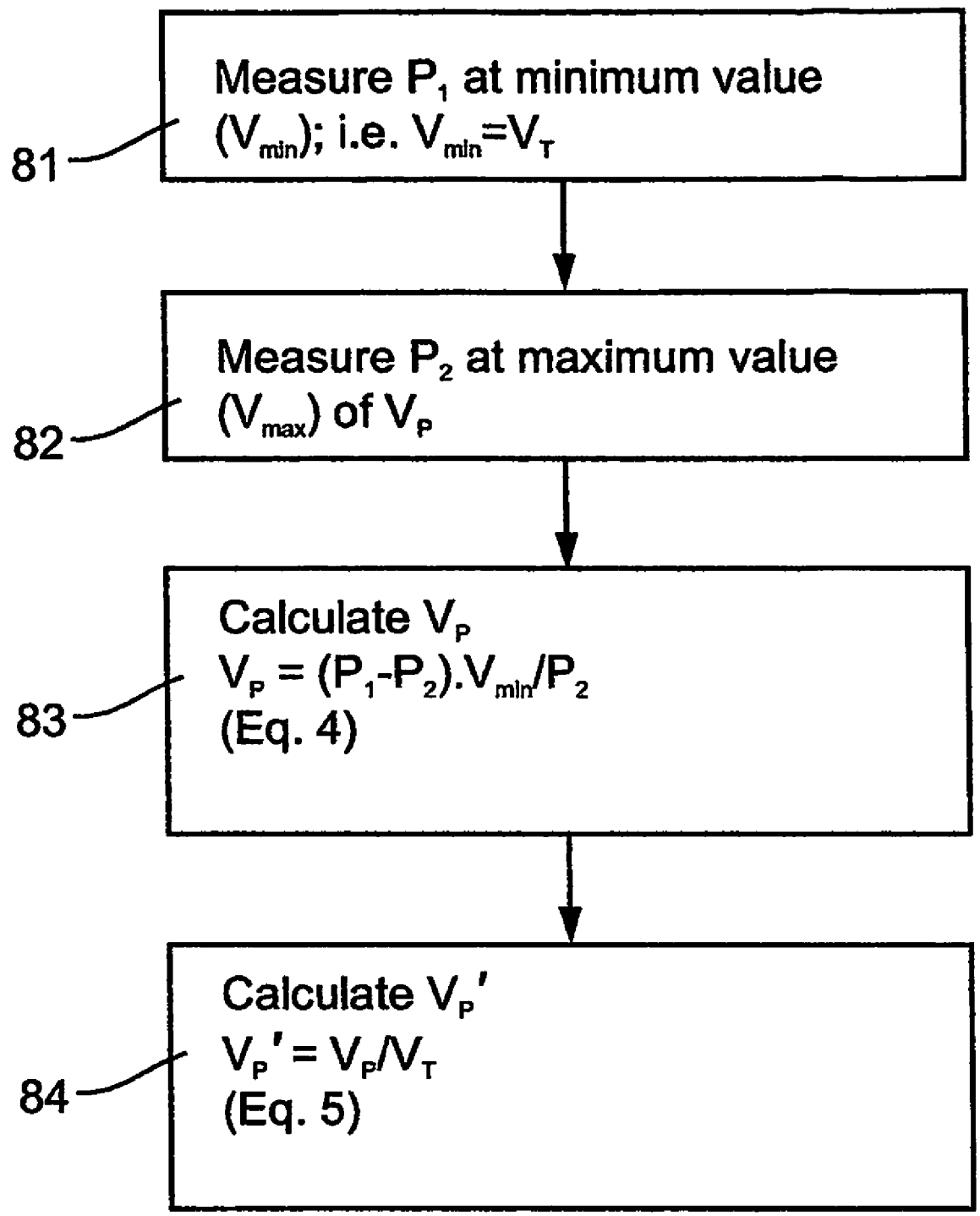
FIG. 7 is a flow chart more particularly illustrating the manner of performing the last two operations in the flow chart of FIG. 2.
Figure 8:
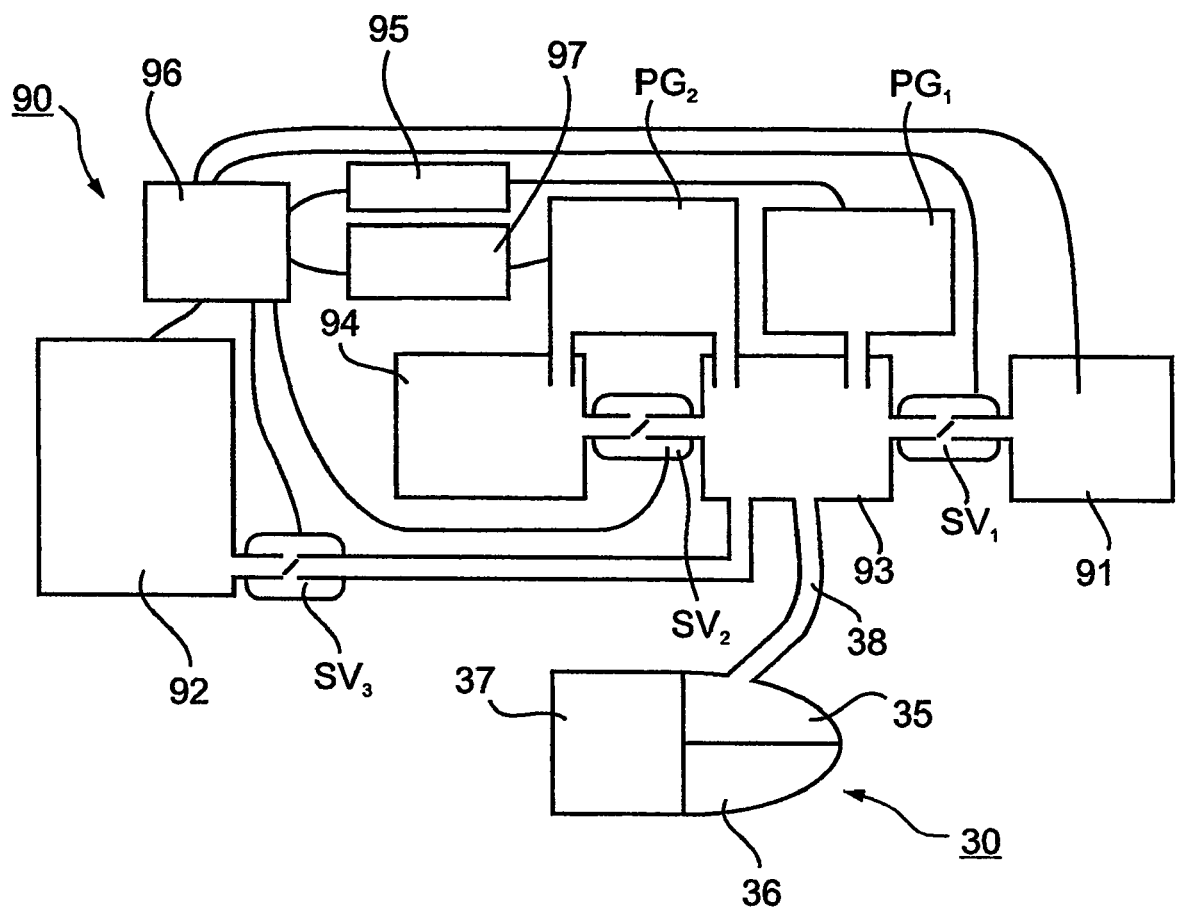
FIG. 8 illustrates one form of apparatus for calibrating, and subsequently operating, the probe of FIG. 1.

A preferred manner of calibrating the probe is illustrated in FIGS. 2-7, whereas apparatus that may be used for this purpose is illustrated in FIGS. 8 and 9.

FIG. 2 is an overall flow chart illustrating one manner of calibrating the probe of FIG. 1 in accordance with the present invention. As shown in FIG. 2, the first operation (block 41) is to measure the volume of the entire compressible fluid system when not applied to the monitored body part. This volume represents the volume $V_S$ in FIG. 1a.

The next operation (block 42) is to measure the volume of the compressible fluid system when applied to the monitored body part. This measured volume, referred to as $V_F$, is equal to $V_S$ reduced by the volume of the non-compressible tissue ($V_T$).

The next operation (block 43) is to calculate the volume ($V_T$) of the non-compressible tissue by subtracting $V_F$ from $V_S$. The correction factor ($C_F$) is considered as the reciprocal of $V_T$ ($1/V_T$) calculated to constitute a calibration factor for the respective patient (block 44). Following determination of the pulse volume (block 45), the correction factor $C_F$ may then be used, as indicated by block 46, to correct the pulse volumes produced by the pressure sensor for a given measurement.

FIG. 3 illustrates one manner of measuring the volume $V_S$ of operation 41 in FIG. 2, namely the volume of the compressible fluid system when not applied to the body part. This procedure involves measuring the pressure $P_1$ of the volume $V_S$ when the compressible fluid system is not applied to the body part (block 51); introducing into the compressible fluid system a known calibrating volume ($V_C$) of the compressible fluid (block 52); measuring the pressure $P_2$ of the volumes $V_S$ and $V_C$ (block 53); and then determining the volume $V_S$ according to the following equation:

$$V_S = P_2 \cdot V_C / (P_1 - P_2) \tag{Eq. 1}$$

Equation 1 can be derived from Boyles Law as follows:

$$P_1 \cdot V_S = P_2 \cdot (V_S + V_C) = P_2 \cdot V_S + P_2 \cdot V_C$$

$$P_1 \cdot V_S - P_2 \cdot V_S = P_2 \cdot V_C$$

$$V_S \cdot (P_1 - P_2) = P_2 \cdot V_C$$

$$V_S = P_2 \cdot V_C / (P_1 - P_2)$$

Figure 5:
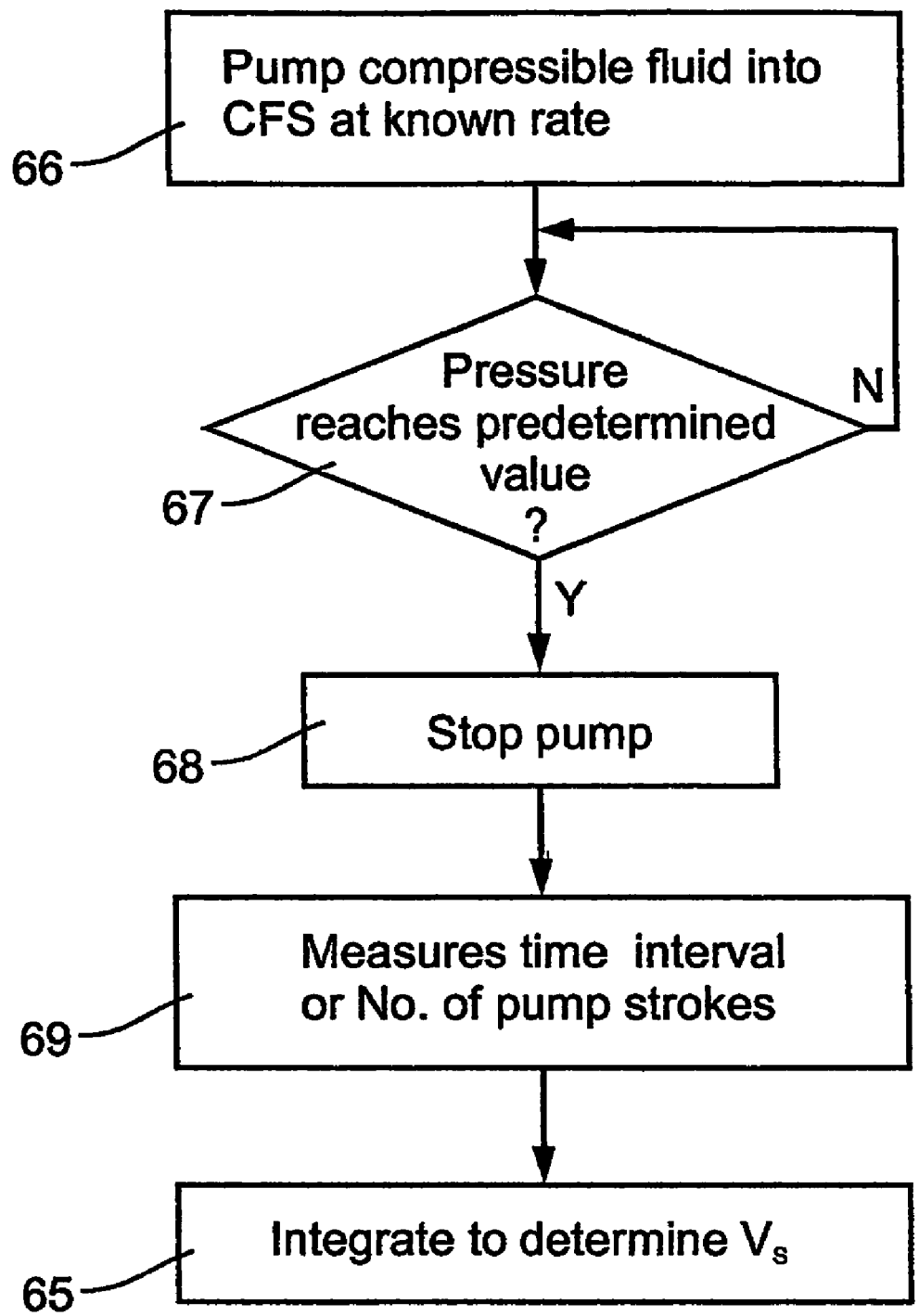
FIG. 5 is a flow chart illustrating the manner of operation of the apparatus of FIG. 4 for performing the first operation in the flow chart of FIG. 2.

The diagram of FIG. 4, and the corresponding flow chart of FIG. 5, illustrate another manner of measuring volume $V_S$ in operation 41 of the flow chart of FIG. 2. Thus, as shown in FIG. 4, the probe, therein generally designated 60, is initially evacuated (such that its initial pressure is zero or below), and is then supplied with the compressible fluid via a pump 61 of known stroke volume for each cycle; alternatively, the system could include a flow regulator 62 maintaining a constant (or known) rate of flow of the fluid into the compressible fluid system of the probe. When a predetermined pressure is detected by a pressure detector 63, the number of strokes, or the flow rate together with the time interval of flow, are inputted into data processor 64, which integrates the flow rate over the time interval from zero pressure to the target pressure to produce the volume $V_S$, as shown at 65. The foregoing operations to produce the volume $V_S$ measurement 65 are shown by blocks 66-69 in the flow chart of FIG. 5.

FIG. 6 is a flow chart illustrating one manner of performing the operations of blocks 42 and 43 in the flow chart of FIG. 2, namely of calculating the volume of the non-compressible tissue ($V_T$) within the probe. This is done by repeating the operations performed in the flow chart of FIG. 3 while the probe is applied to the monitored body part, such that the operation of measuring the pressure $P_1$ (block 71) is the same as that in block 51 of FIG. 3, but the operation of measuring the pressure $P_2$ (block 72) is performed with respect to the compressible fluid volume $V_F$ plus the calibrating fluid volume $V_C$.

The following calculation, indicated by block 73 in FIG. 6, is performed which determines $V_F$ (rather than $V_S$ in block 54, FIG. 3).

$$V_F = P_2 \cdot (V_F + V_C) / (P_1 - P_2) \tag{Eq. 2}$$

As shown by block 74, once $V_S$ and $V_F$ have been determined, the volume $V_T$ (of the non-compressible tissue) can be determined according to the following equation:

$$V_T = V_S - V_F \tag{Eq. 3}$$

FIG. 7 is a flow chart illustrating one manner of performing operation 44 in the flow chart of FIG. 2, namely of quantitatively calculating the pulse volume $V_P$, and of operation 46 of FIG. 2, namely of quantitatively calculating the corrected pulse volume $V_P'$ expressed with respect to the tissue volume $V_T$ for the given measurement. As shown in FIG. 7, this operation is performed by: measuring the pressure $P_1$ at the minimum value ($V_{min}$) of the sensed pressure pulse $V_P$, representing the instantaneous volume due to the pulsatile arterial blood flow to the body part (block 81); then measuring pressure $P_2$ as the maximum value ($V_{max}$) of the sensed pressure pulse (block 82); calculating (per block 83) the pulse volume ($V_P$) according to the following equation:

$$V_P = (P_1 - P_2) \cdot V_{min} / P_2 \tag{Eq. 4;}$$

where $V_{min} = V_T$; and finally calculating $V_P'$, the pulse volume corrected for the particular patient, by using the calibration factor $C_F = 1/V_T$, as follows:

$$V_P' = V_P / V_T \tag{Eq. 5}$$

Equation 4 in operation 83 above, for calculating the pulse volume $V_P$ can be derived as follows:

$$P_1 \cdot V_{min} = P_2 \cdot (V_{max})$$

where $P_1$, $P_2$, and $V_{min}$ are known, and $V_P = V_{max} - V_{min}$;

$$P_1 \cdot V_{min} (\text{i.e., } V_T) = P_2 \cdot (V_{min} (\text{i.e., } V_T) + V_P) = P2\, V_{min} + P_2 \cdot V_P$$

$$P_1 - P_2 \cdot V_{min} (\text{i.e. } V_T) = P_2 \cdot V_P (\text{i.e., } V_T) + P_2 \cdot V_P$$

$$V_P = (P_1 - P_2) \cdot V_{min} (\text{i.e., } V_T) / P_2 \tag{Eq. 4}$$

As indicated by operation 84 above, the value of the pulsatile volume can thus be expressed as a fraction of the tissue volume from which it is derived, so as to provide an index of pulse size corrected for tissue volume.

FIG. 8 illustrates one form of apparatus that may be used for calibrating probe 30 of FIG. 1 in the manner described above in accordance with the physical characteristics, particularly the tissue volume, of the particular patient's body part monitored by the probe, before using the probe for detecting medical conditions in the particular patient by sensing and quantifying the arterial pulse volume, or volume-related, changes in the respective body part in either absolute and relative terms. The apparatus illustrated in FIG. 8 uses the compressible fluid system described in the above-cited U.S. Pat. No. 6,319,205 (FIG. 9) for sensing the volume changes in the body part (e.g., patient's finger). The illustrated apparatus includes an air pressure source 91 as in the above cited U.S. Pat. No. 6,319,205, but also includes a calibrated volume source 92 for introducing the calibrated volume ($V_C$) of the fluid during the calibration process, as described above, particularly with respect to the flow chart of FIG. 3. To simplify the description, FIG. 8 does not include the connection of the static pressure chamber (37, FIG. 1) to the compressible fluid system, it being appreciated that such a connection would include a tube (not shown) from port 37a (FIG. 1) to the pressure source 91.

As shown in FIG. 8, chambers 35, 36 (FIG. 1) of probe 30, which sense the volume changes in the patient's finger due to pulsatile arterial blood flow therein, are connected by a tube 38 to a probe reservoir 93. Reservoir 93 is in turn connected: to pressure source 91, via a first solenoid valve $SV_1$; to a reference reservoir 94, via a second solenoid valve $SV_2$; and to the calibrated volume source 92, via a third solenoid valve $SV_3$. The probe reservoir 93 further includes a pressure gauge $PG_1$ having an electrical output connected via an amplifier 95 to a data processor CPU 96. A differential pressure gauge $PG_2$ detects the differential pressure between the probe reservoir 93 and the reference reservoir 94 and produces an electrical output via amplifiers and filter 97 to CPU 96. It will be appreciated that CPU 96 includes, not only the data processor, but also the A/D inputs to the data processor, as well as the monitor and alarm outputs from the data processor, as more particularly illustrated in FIG. 9 of U.S. Pat. No. 6,319,205.

The operation of the apparatus illustrated in FIG. 8 is basically the same as that described in U.S. Pat. No. 6,319,205 with respect to FIG. 9 of that Patent, it being appreciated that the solenoid valve $SV_3$ is opened in order to introduce the calibrated volume $V_C$ from source 92 into the fluid of the system for purposes of calibrating the probe as described above with respect to the flow chart of FIG. 3.

An alternative way of quantitatively evaluating pulsatile volume changes due to arterial blood changes in the tissue within the system would be to use the calibrated volume generating source 92, under the control of CPU 90, and using feedback from pressure gauges PG1 and PG2, to maintain a constant pressure as determined by both differential pressure transducer PG2, and gauge pressure transducer PG1. In this manner, volume changes which are equal in size to and opposite in direction to those produced by the body part are generated, and their measurement would thus correspond to the actual volume changes of the arterial pulsatile changes.

A further way in which the system illustrated in FIG. 8 can be used to quantify observed volume changes, would be to use the calibrated volume generating source 92, under the control of CPU 90, and using feedback from pressure gauges PG1 and PG2 to generate known volume changes which produce pressure changes matching those of the observed pulsatile changes.

FIG. 9 illustrates apparatus, similar to that of FIG. 8 but including, instead of the calibrated volume source 92, a manually-operated syringe, generally designated 100, for introducing the volume of calibrating fluid ($V_C$, per the flow chart of FIG. 3) into the compressible fluid system to permit manual calibration of the apparatus. Thus, syringe 100 includes a tubular housing 101 open at one end for receiving a manually-depressible plunger 102, and closed at the opposite end except for an outlet port 103. Plunger 102 is outwardly biased to a normal state as illustrated in FIG. 9a by a spring 104, but is manually depressible to a depressed state as illustrated in FIG. 9b to introduce a defined calibrating volume ($V_C$) of fluid into the reservoir 93 via outlet port 103.

Syringe 100 illustrated in FIGS. 9, 9a and 9b further includes an electrical switch SW which is actuated by depression of plunger 102, to thereby inform CPU 90, via its electrical connection 105, of the introduction of the calibrating volume of fluid into the compressible fluid system.

Figure 9C:
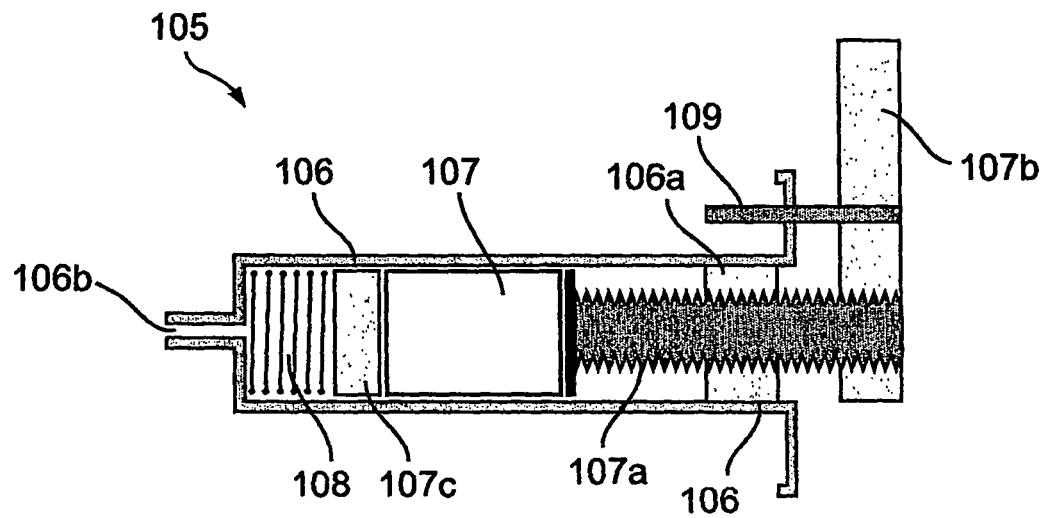
FIG. 9c is a longitudinal sectional view illustrating another construction of manually-operated syringe that may be used in the apparatus of FIG. 9 for introducing the calibrating fluid.

FIG. 9c illustrates another construction of manually-operated syringe, generally designated 105, which may be used in the apparatus of FIG. 9 for introducing the calibrating fluid. Syringe 105 includes a tubular housing 106 having an open end occupied by a nut 106a, the opposite end of the housing being closed except for an outlet port 106b. Syringe 105 further includes a plunger 107 having a threaded stem 107a rotatably received within nut 106a, and a handle 107b fixed to the threaded stem outwardly of the housing 106. The inner end of plunger 107 includes a seal 107c defining an expansible/contractible compartment between it and the housing outlet port 106b, which compartment is to be filled with the calibrating fluid to be introduced into the apparatus of FIG. 9. Plunger 107 is outwardly biased by a spring 108 interposed between the plunger seal 107c and the end wall of the housing 106.

Figure 9D:
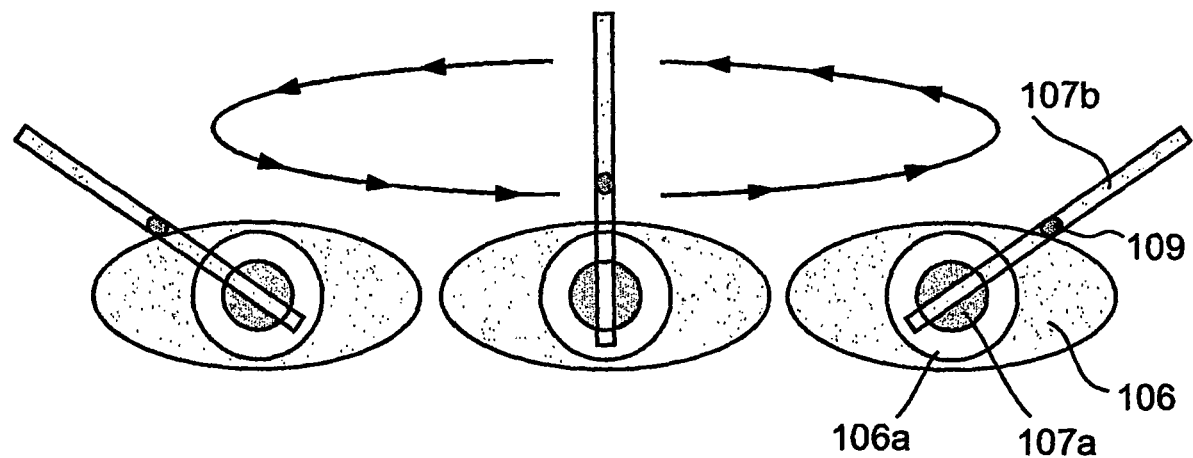
FIG. 9d are three end views illustrating three positions of the handle in the manual syringe of FIG. 9c.

It will be seen that handle 107b may be shifted back and forth through the cyclic range depicted by the arrows in FIG. 9d (three positions of which are illustrated in FIG. 9d), so as to define the volume of the fluid chamber between the plunger seal 107c and the housing outlet port 106b, and thereby the volume of the calibrating fluid introduced into the apparatus of FIG. 9. Handle 107b thus provides a simple way of producing bi-directional, defined volume changes. It can also be used to generate a wave-form resembling the pulse-upstroke. Handle 107b may be provided with an inwardly-directed pin 109 riding on a cam surface in the housing 106 so as to restrict the range of motion of the handle to predefined limits during its rotatable movements.

As described above, the accurate determination of the tissue volume ($V_T$) of the body part in the respective patient monitored by the probe is important for evaluating the pulsatile volume change relative to the tissue mass from which it is taken since this improves the accuracy, as well as the reproducibility of the measurements for the respective patient. The knowledge of the tissue volume ($V_T$) for the respective measurement is also very important because it can substantially affect the gain of the pressure measuring system. As the relative volume of tissue (non-compressible) in the body part monitored by the probe increases, there is a corresponding decrease in the effective residual volume of the compressible fluid in the measuring system, and therefore a corresponding increase in the pressure swings resulting from a given pulsatile volume change of the tissue within the system.

Figure 10:
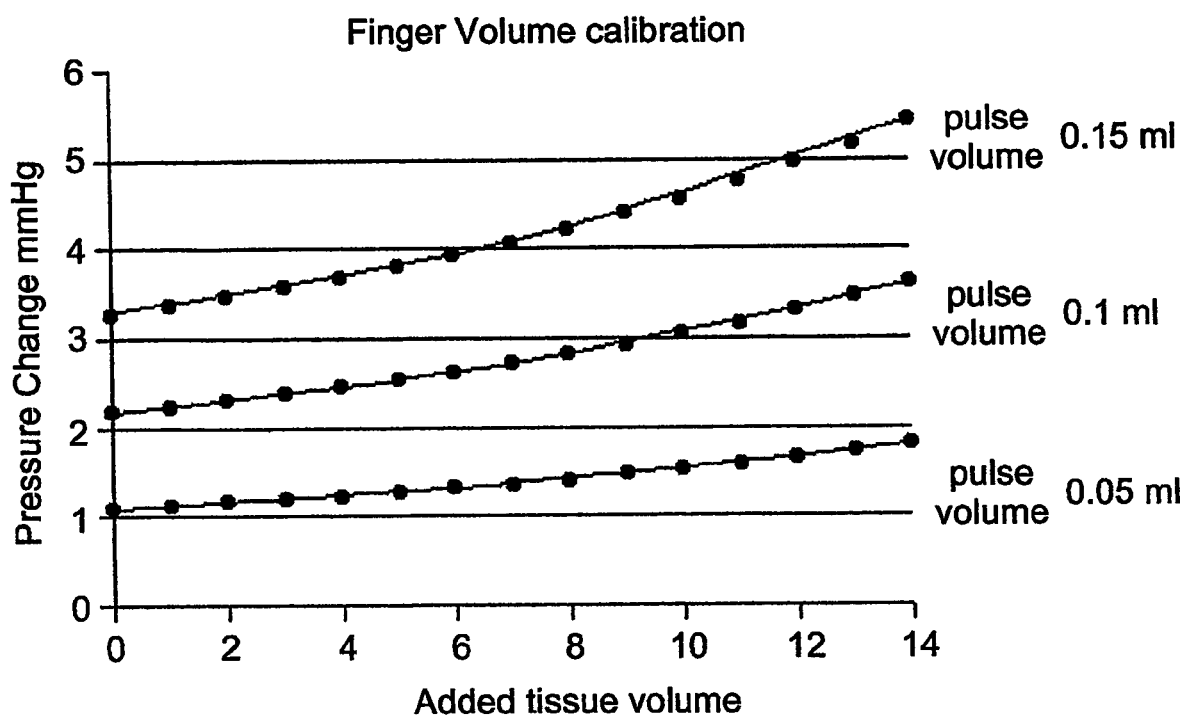
FIG. 10 illustrates how the system's pressure-volume characteristics are affected by the body part's tissue volume when using the probe of FIG. 1.

FIG. 10 illustrates pressure changes associated with volume swings of 0.05, 0.10 and 0.15 ccm volume occurring within a range of added tissue volumes from 0 to 14 ccm when the overall system volume is 35 ccm. This figure thus illustrates how the system's pressure volume characteristics are affected by the tissue volume ($V_T$) with respect to the overall volume of the fluid system ($V_S$) which includes not only the volume of the tissue $V_T$, but also the volume of the compressible fluid ($V_F$), as described above with respect to the flow charts of FIGS. 4-7.

The accuracy of the measured volume of the non-compressible tissue ($V_T$), and that of the pulsatile volume $V_P$ may be verified by repeating the calibrating procedure described above with respect to FIGS. 3-7 while using instead of the body part (e.g., finger) of the patient, a physical model of a known fixed volume, preferably with the added ability of generating pulses of defined volume.

Figure 11A:
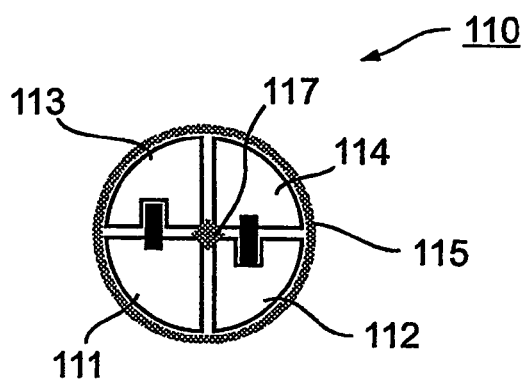
FIGS. 11a and 11b are axial and longitudinal views, respectively, illustrating an adjustable physical model which may be used for verifying the calibration of a probe in accordance with the present invention.
Figure 11C:
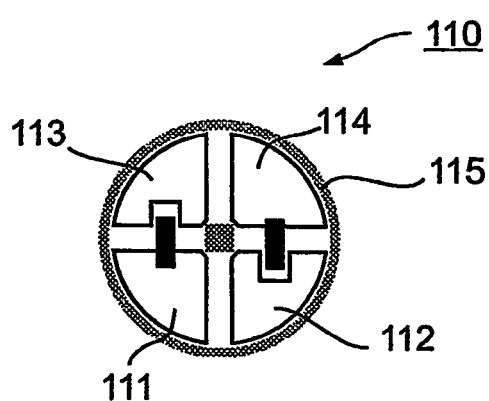
FIGS. 11c and 11d are views corresponding to those of FIGS. 11a and 11b, respectively, but illustrating a different adjusted position of the physical model.
Figure 11B:
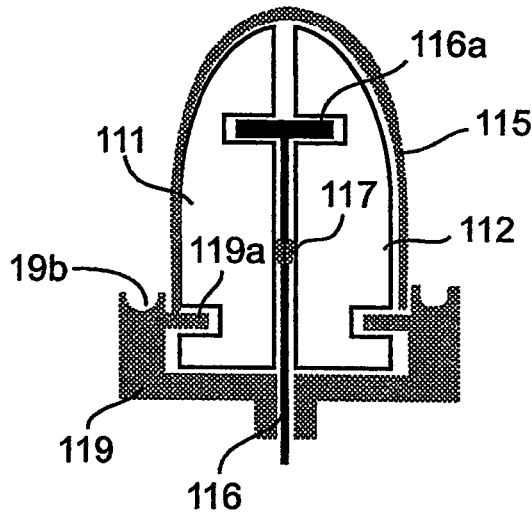
Figure 11D:
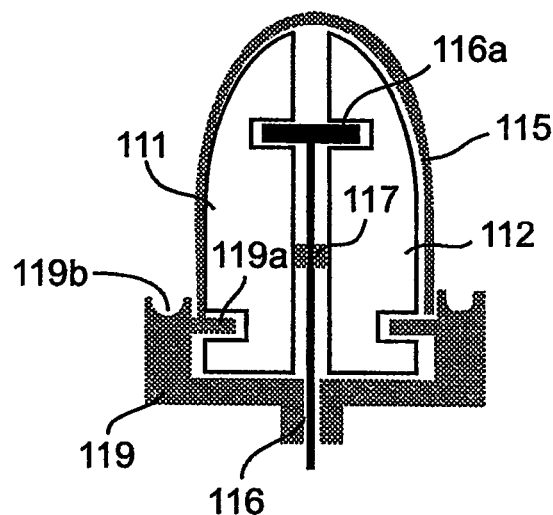

FIGS. 11a-11d illustrate a construction of such a physical model corresponding generally to the shape and size of the body part and capable of changing its volume to enable its use for also verifying the accuracy of the pulsatile volume calibration. FIGS. 11a and 11b are plan and side views, respectively, illustrating the physical model, therein generally designated 110 to define one volume, and FIGS. 11c and 11d are corresponding views illustrating the physical model defining a larger volume.

Physical model 110 includes an assembly of four model sections 111-114 enclosed within an outer elastic envelope 115 configured and dimensioned to generally simulate the end of a patient's finger to be introduced into the probe (30, FIG. 1). Physical model 110 further includes a central shaft 116 carrying a cam 117 engageable with the inner surfaces of the model sections 111-114 so as to space them further apart or closer together, according to the rotation of the shaft, this being permitted by the elasticity of the outer envelope 115. The inner end of the shaft 116 preferably includes an enlarged head 116a received within recesses on the inner faces of the model sections 111-114 for guiding the movements of the model sections with respect to the shaft. In addition, the inner faces of two of the model sections 111, 114 preferably include pins 118 receivable within recesses in the corresponding surfaces of the other two model sections 112, 113, for guiding the movements of the model sections relative to each other.

Physical model 110 further includes a holder 119 for holding the four model sections 111-114, and the elastic outer envelope 115 enclosing them. Holder 119 includes an inner annular flange 119a received within an annular recess formed on the outer surfaces of the model sections 111-114, for retaining them within the assembly. Holder 119 also includes an annular groove 119b for receiving the probe 30 (FIG. 1) when the model is used for verifying the calibration of the probe for the particular patient, as described above.

Figure 12A:
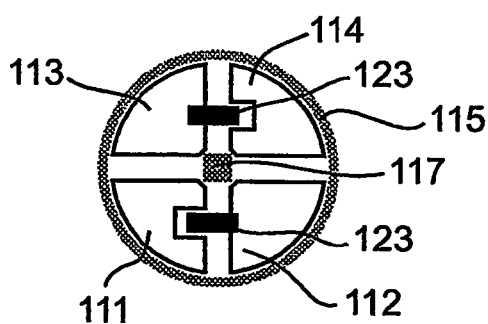
FIGS. 12a and 12b are views corresponding to those of FIGS. 11a and 11b, respectively, but illustrating a modification in the construction of the physical model.
Figure 12B:
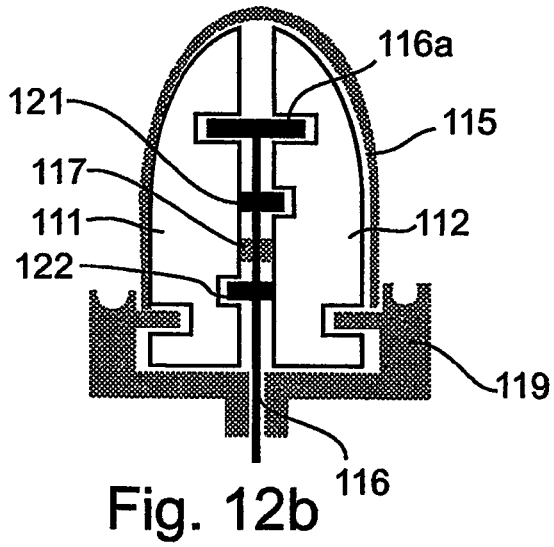

FIGS. 12a and 12b are views, corresponding to those of FIGS. 11a and 11b, of a physical model of similar structure but including a slightly different arrangement of guiding elements for guiding the movements of the model sections 111-114 towards or away from each other by the rotation of the shaft 116. Thus, as shown in FIGS. 12a and 12b, the shaft 116 includes, in addition to the cam 117 for effecting the movements of the model sections, and the enlarged head 116a for guiding the movements of the sections, further guiding elements, as shown at 121 and 122 for guiding the movements of the model sections. In addition, two of the model sections include a slightly different arrangement of pins 123 receivable within recesses in the other two model sections for guiding the movements of the model sections with respect to each other.

Figure 13:
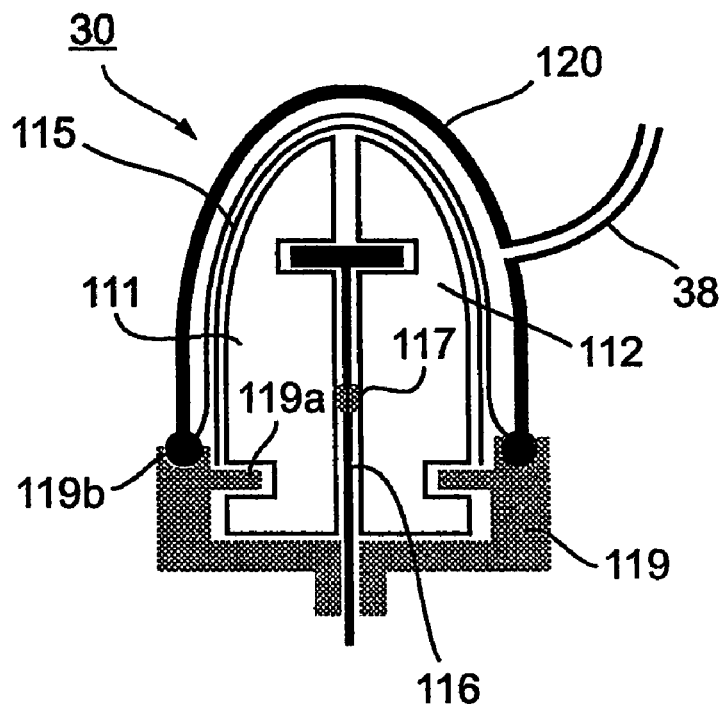
FIG. 13 illustrates one manner of using the physical model of FIGS. 11a-11d for calibrating a pressuring-sensor type probe in accordance with the present invention.

FIG. 13 illustrates a probe 30 including physical model 110 of FIGS. 11a-11d housed within casing 120. Casing 120 is mounted within annular grove 119b of holder 119 of physical model 110, for using the physical model in order to verify the calibration of both tissue volume and pulsatile volume for the system.

Figure 14:
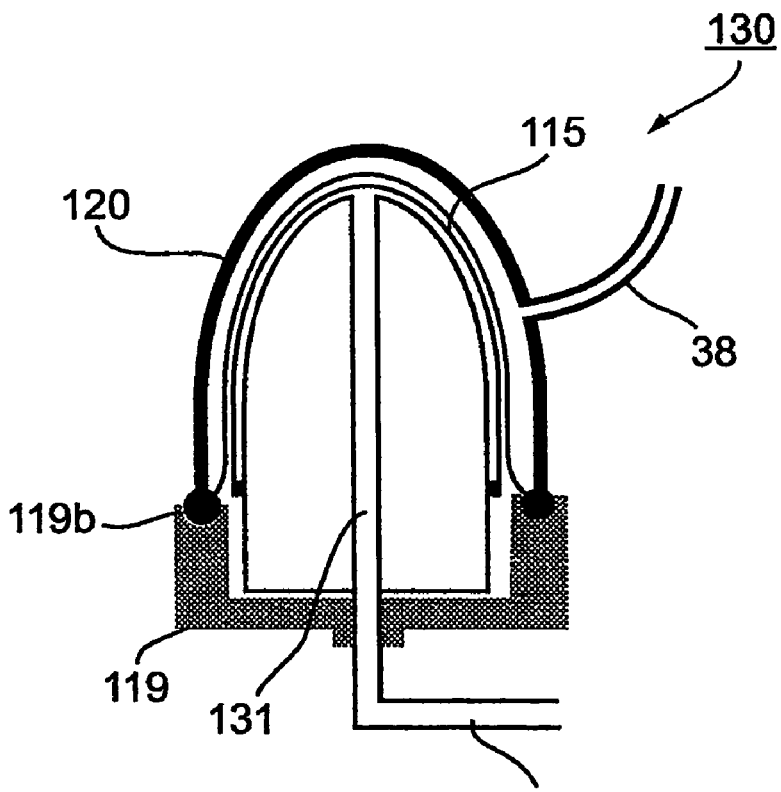
FIG. 14 illustrates another type of physical model which may be used for calibrating a pressure-sensor type probe.

It will be appreciated that the physical model constructions described above are merely illustrative of designs that can be used for this purpose, and that many other designs can also be used to achieve the predetermined volume change effect. FIG. 14 illustrates another construction of a physical model, therein designated 130, similar to those described above except that, instead of using a rotary shaft and cam (116, 117) for effecting the movements of the model sections with respect to each other, there is used instead an inflatable bladder 131. Bladder 131 extends centrally of the assembly of model sections such that the inflation or deflation of the bladder will displace the model sections away or towards each other in order to change the volume enclosed within the elastic envelope 115 to produce the desired calibrating volume ($V_C$). For example, the physical model 130 illustrated in FIG. 14 could be used with the apparatus illustrated in FIG. 9, in which case the syringe 100 of FIG. 9 would be coupled to the inflatable bladder 131 of the physical model.

An alternative way in which the device illustrated in FIG. 14 could be used is to have all the model sections maintained in fixed position with respect to the central passage, but allowing the external elastic envelope 115 to accommodate the volume displacements brought about by the syringe 100 of FIG. 9.

Calibrating an Optical-Sensor Type Probe (FIGS. 15-18)

Figure 15:
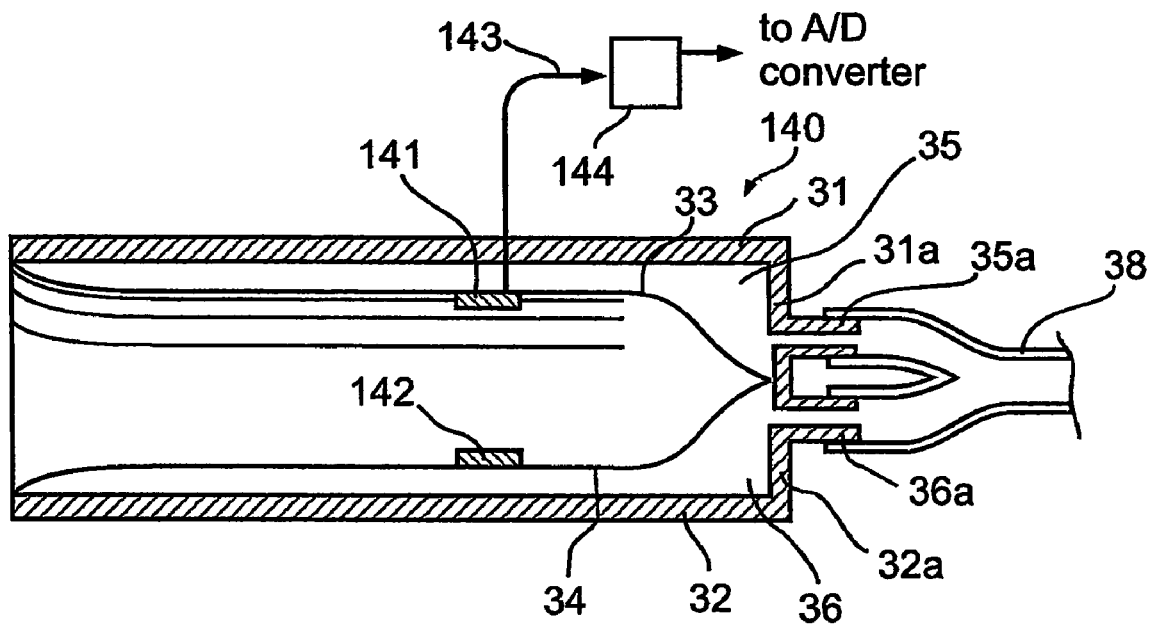
FIG. 15 illustrates an optical-sensor type probe which may be calibrated in accordance with the present invention.

FIG. 15 illustrates an optical-sensor type probe described in U.S. Pat. No. 6,319,205 (FIG. 15) which may also be calibrated in accordance with the present invention for the particular patient in order to improve the diagnostic capability and/or the reproducibility of the measurements when the probe is used for detecting various medical conditions.

The probe illustrated in FIG. 15, therein generally designated 140, may be constructed as described above with respect to FIG. 1, except that its membranes 34, defining a tubular socket for receiving the patient's finger, carry a light source 141 and a light receiver 142 to detect pulsatile blood volume changes in the finger as changes in optical density by the light receiver 142. The electrical output of the probe is fed via conductors 143 to an amplifier circuit 144, where it is amplified and filtered, and then fed to the data processor, (e.g., CPU 96, FIG. 8) for processing. Further details of the construction and operation of the probe, and the manner of processing its output to detect various medical conditions, are set forth in the above-cited U.S. Pat. No. 6,319,205. It will be appreciated that the optical sensor elements 141, 142 could be used either independently of the volumetric sensing means described above for sensing changes in volume of chambers 35, 36, or together with such volumetric sensing means.

The optical probe illustrated in FIG. 15 can be calibrated, or its calibration in the manner described above can be verified, by the use of an optical model which produces, in the light receiver 142, a waveform simulating that produced by the pulsatile arterial blood flow in the finger of the respective patient.

Figure 16:
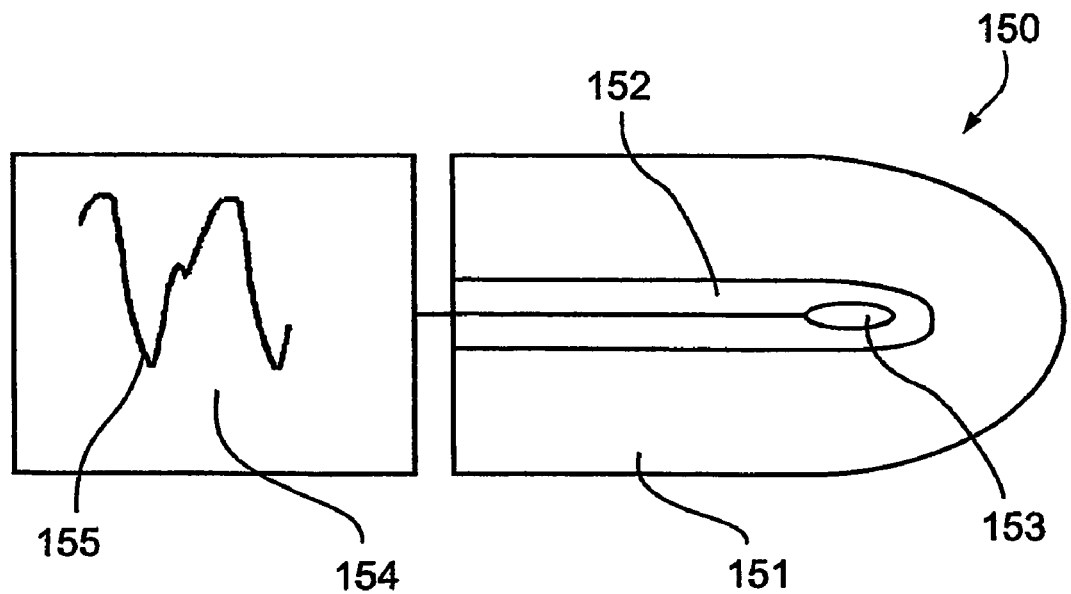
FIG. 16 diagrammatically illustrates a physical model which may be used for calibrating the optical-sensor probe of FIG. 15.

One such optical model is illustrated in FIG. 16, generally designated 150. Model 150 includes a body 151 of light-transmissive, (e.g., translucent) material simulating the shape and dimensions of the body part, (e.g., the patient's finger) to be received within the optical probe (140, FIG. 15). Model 150 further includes a removable unit containing a light source 153 driven by a function generator 154 which is capable of generating waveforms 155 simulating the optical density changes accompanying the pulse wave in the given body part (e.g., finger) of the patient being monitored by the probe.

It will be appreciated that the optical density of the patient's finger received within the probe is increased when there is an increase in the volume of blood, such as during the systolic phase of the cardiac cycle. This results in greater light absorption, and consequently less light transmission. Thus, the simulation waveform generates a relatively lower level of light intensity during the systolic phase of the cardiac cycle.

On the other hand, during the diastolic phase of the cardiac cycle, there is less blood in the finger, and therefore its optical density is lower. Accordingly, the simulation waveform generates a relatively higher level of light intensity during the diastolic phase.

Figure 17:
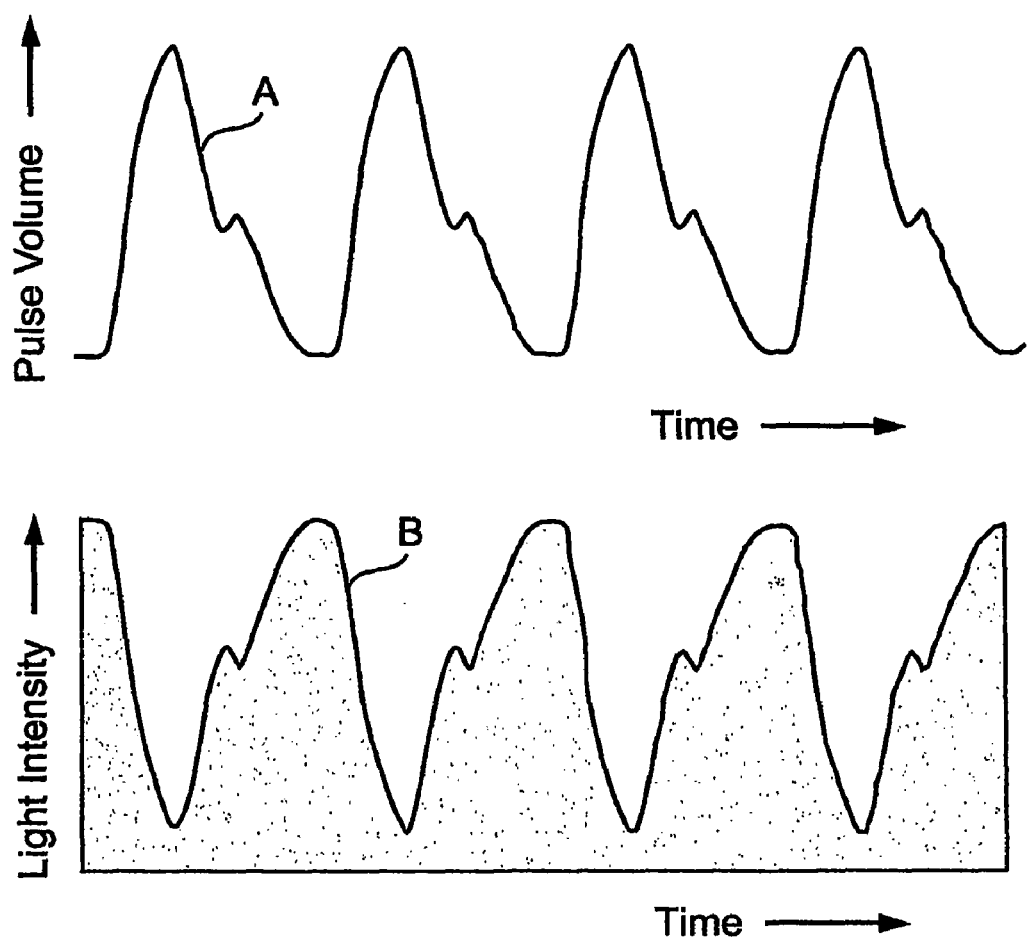
FIG. 17 illustrates the light-density/pulse-volume relationship when calibrating an optical-sensor type probe.

FIG. 17 illustrates the inverse relationship between the blood volume (trace A) and light intensity (trace B) described above. Such a basic pattern can be modified or amplified, or its rate can be changed, as required for the particular patient. The optical characteristics of the optical body 151 can also be varied, as can also the optical characteristics of the light source 152, such as intensity and spectral composition. In addition, the signal from the function generator 153 could also be used to drive a motor for producing physical pulse waves suitable for use with the physical model described above with respect to FIGS. 11a-14.

Figure 18:
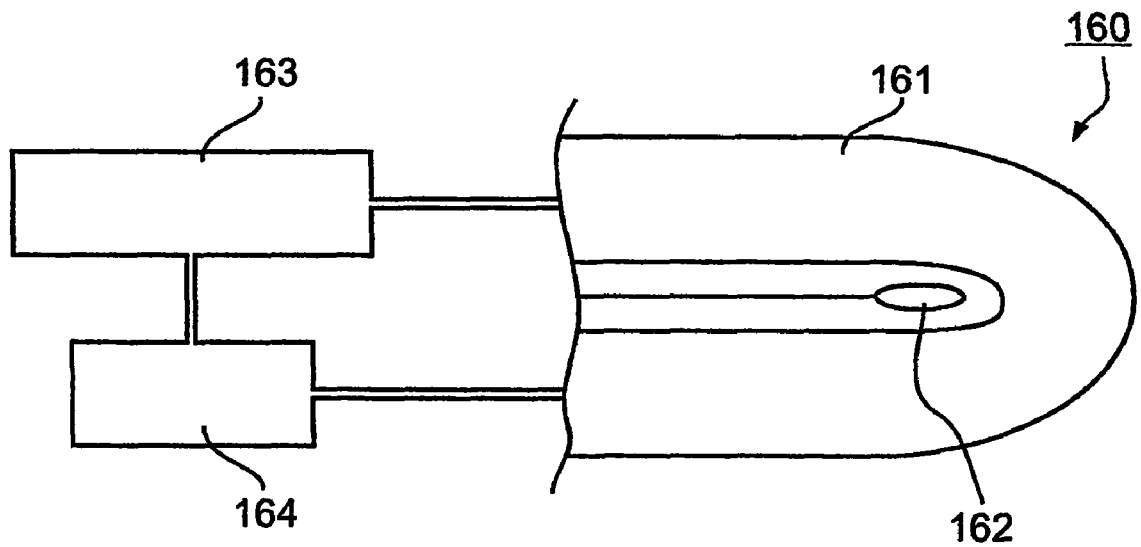
FIG. 18 diagrammatically illustrates another physical model which may be used for calibrating an optical sensor probe.

FIG. 18 illustrates another form of optical model which can be used for calibrating the optical-sensor type probe of FIG. 15. The optical model illustrated in FIG. 18, therein generally designated 160, also includes an optical body 161 also simulating the form and dimensions of the patient's finger to be monitored, and also including a light source 162 within body 161. In this case, however, optical body 161 is constituted of a porous matrix through which a liquid light absorbing medium is to be pumped, simulating the vascular bed of the tissue in the patient's finger to be monitored. Thus, as shown in FIG. 18, a light absorbing liquid is pumped from a reservoir 163 by a pump 164 through the porous matrix of body 161 to vary the amount of the light absorbing liquid within the matrix in a manner analogous to the pulsatile blood volume changes occurring in the patient's finger.

It will be appreciated that the optical model illustrated in FIG. 18, as well as that in FIG. 16, could be used for both optical density and physical volumetric calibration procedures. Such a device could also be used to provide a volumetric calibration of an optical-sensor type probe, e.g., by separately determining the physical volume of the pumps liquid, as well as its optical absorption characteristics relative to blood.

It will also be appreciated that in the case of volumetrically based calibrations of any of the above described values (i.e., $V_S$, $V_F$, $V_T$ or $V_{min}$, $V_{max}$, $V_P$, and $V_C$), in order to facilitate standardization of the measured values, the resulting values may need to be corrected to some predetermined set of conditions of atmospheric pressure and temperature. Such correction may be performed by including appropriate temperature and barometric pressure meters (not shown) in FIG. 8 or 9, and using standard correction equations for the correction of gas volumes to conventionally accepted conditions such as standard STP (standard temperature and pressure) or ATP (ambient temperature and pressure).

While the invention has been described with respect to several preferred embodiments, it will be appreciated that these are set forth merely for purposes of example, and that many other variations, modifications and applications of the invention may be made.

What is claimed is:

1. A method of improving the diagnostic performance of a probe system for detecting a medical condition in a patient, which probe system includes at least one probe to be applied to a measurement site of the patient for sensing volume or volume-related changes in a monitored body part thereat due to pulsatile arterial blood flow in the body part, comprising:

providing a probe that includes a pressure sensor which senses said volume changes by sensing changes in pressure in a compressible fluid system of volume $V_F$ when applied to said monitored body part and of volume $V_S$ where not applied to said body part, said body part including a fixed volume $V_T$ of non-compressible tissue and a pulsitatively-variable volume $V_P$ corresponding to arterial volume changes, such that the pressure in said compressible fluid system changes with the change in pulsatile volume thereof and the gain of said changes varies according to the relative values of the volumes $V_T$ and $V_F$;

calibrating said probe system for the respective measurement site of the respective patient according to a predetermined characteristic of said monitored body part of the patient; and quantifying the arterial pulsatile volume thereat using a data processor.

2. The method according to claim 1, wherein the relation values of the volumes $V_T$ and $V_F$ are determined by:

determining the volume $V_S$ of said compressible fluid system when it is not applied to the body part;

determining the volume $V_F$ of the compressible fluid system when it is applied to the body part;

and subtracting $V_F$ from $V_S$ to produce the volume $V_T$ of the non-compressible tissue.

3. The method according to claim 2, wherein the volume $V_S$ of the compressible fluid system when it is not applied to the monitored body part is determined by:

measuring the pressure ($P_1$) of said volume $V_S$ of the compressible fluid system when it is not applied to the monitored body part;

introducing into said compressible fluid system a known calibrating volume ($V_C$) of the compressible fluid;

measuring the pressure ($P_2$) of said volumes $V_F$ and $V_C$;

and determining the volume $V_S$ of the compressible fluid system according to the following equation:

$$V_S = P_2 \cdot V_C / (P_1 - P_2) \qquad \text{(Eq. 1)}.$$

4. The method according to claim 3, wherein the volume $V_S$ of said compressible fluid system when it is not applied to the monitored body part is determined by:

introducing said compressible fluid into the compressible fluid system at a known rate;

measuring the time taken for the pressure in the compressible fluid system to reach a predetermined value;

and integrating said known rate over said measured time.

5. The method according to claim 3, wherein the effective volume $V_F$ of the compressible fluid system when it is applied to the monitored body part and effective volume $V_T$ of the non-compressible tissue is determined by:

measuring the pressure ($P_1$) of the volume $V_F$ of the compressible fluid system when it is applied to the monitored body part;

measuring the pressure $P_2$ of the volumes $V_F$ and $V_C$ of the compressible fluid system after introducing said calibration volume $V_C$;

determining the volume $V_F$ of the compressible fluid system when it is applied to the monitored body part according to the following equation:

$$V_F = P_2 \cdot V_C / (P_1 - P_2) \qquad \text{(Eq. 2)}$$

and determining the volume $V_T$ of the non-compressible tissue according to the following equation:

$$V_T = V_S - V_F \qquad \text{(Eq. 3)}.$$

6. The method according to claim 5, wherein said probe outputs a pulsatile signal corresponding to said sensed arterial volume changes $V_P$, and wherein said pressures $P_1$ and $P_2$ are $P_{min}$ and $P_{max}$ taken, respectively, at the lowest and highest points of the pulsatile signals outputted by said probe.

7. The method according to claim 6, wherein the pulse volumes $V_P$ are determined according to the following equation:

$$V_P = (P_1 - P_2) \cdot V_{min} / P_2 \qquad \text{(Eq. 4)}$$

wherein: $V_{min} = V_T$; and $P_1 = P_{min}$ and $P_2 = P_{max}$.

8. The method according to claim 7, wherein said pulse volumes $V_P$ are multiplied by the fraction $K/V_T$ (K being a constant), and are used as an index of pulse size corrected for the tissue volume of the respective patient.

9. The method according to claim 5, wherein the method further includes verifying the accuracy of the measured volume of the pulsatile signal corresponding to said sensed arterial volume changes $V_P$ by repeating the foregoing operations while applying the compressible fluid system, instead of to the body part, to a physical model of a known fixed volume having the ability of generating pulses of defined volume.

10. The method according to claim 3, wherein the probe system is calibrated while the temperature and barometric pressure are measured at the time of calibration, and during subsequent measurements, and all derived volumes are expressed in terms of a set of predetermined standard conditions of atmospheric pressure and temperature.

11. The method according to claim 10, wherein said probe is calibrated by means including:

a pressure sensor;

a pump for introducing said compressible fluid into the compressible fluid system of the probe system from a calibrated volume generating source;

and a data processor for determining the total added volume and the time taken for the pressure in the compressible fluid system to reach a predetermined pressure value.

12. The method according to claim 11, wherein said calibrated volume generating source, said pressure sensor, and said data processor maintain a constant pressure within said probe system, such that volume changes generated by the said calibrated volume generating source are equal in size but opposite in direction to volume changes in said monitored body part due to pulsatile arterial blood flow in the monitored body part.

13. The method according to claim 1, wherein said monitored body part is a finger, toe or distal portion of a limb of the patient, and said probe encloses said body part such as to monitor the peripheral arterial tone thereof.

14. A method of improving the diagnostic performance of a probe system for detecting a medical condition in a patient, which probe system includes at least one probe to be applied to a measurement site of the patient for sensing volume or volume-related changes in a monitored body part thereat due to pulsatile arterial blood flow in the body part comprising,
providing a probe that includes an optical sensor having a light source and a light receiver;
wherein said probe is calibrated for the respective patient by the use of a model which modifies said light source to produce in said light receiver a waveform simulating that produced by the pulsatile arterial blood flow in the monitored body part of the respective patient,
calibrating said probe system for the respective measurement site of the respective patient according to a predetermined characteristic of said monitored body part of the patient, and
quantifying the arterial pulsatile volume thereat using a data processor.

15. The method according to claim 14, wherein said model includes a light-transmissive body illuminated by said light source, and a function generator for generating a waveform to drive said light source such as to produce in said light receiver a waveform simulating that produced by the pulsatile arterial blood flow in the monitored body part of the respective patient.

16. The method according to claim 15, wherein said model includes:
a porous light-transmissive matrix simulating the vascular bed of the non-compressible tissue in the monitored body part of the respective patient;
a liquid light-absorbing medium;
and a pump for pumping said liquid light-absorbing medium through said porous matrix in a manner analogous to the pulsatile arterial blood flow through the monitored body part of the respective patient.

17. Apparatus for detecting a medical condition of a patient, comprising:
a probe system including a probe to be applied to a measurement site of the patient for sensing volume or volume-related changes in a monitored body part thereat due to pulsatile arterial blood flow in the body part;
and calibrating means for calibrating said probe system for the respective measurement site, according to a predetermined physical characteristic of the body part of the respective patient, and for quantifying the arterial pulse volume thereat;
wherein said probe includes a pressure sensor which senses said volume changes by sensing changes in pressure in a compressible fluid system of volume $V_F$ when applied to said monitored body part and of volume $V_S$ where not applied to said body part, said body part including a fixed volume $V_T$ of non-compressible tissue and a pulsitatively-variable volume $V_P$ corresponding to arterial volume changes, such that the pressure in said compressible fluid system changes with the change in pulsatile volume thereof and the gain of said changes varies according to the relative values of the volumes $V_T$ and $V_F$.

18. The apparatus according to claim 17, wherein said calibrating means includes a data processor programmed to determined the volume $V_S$ of the compressible fluid system according to the following equation:

$$V_S = P_2 \cdot V_C/(P_1 - P_2) \quad \text{(Eq. 1)}$$

wherein:
$P_1$ is the pressure of the compressible fluid system, of volume $V_F$, when it is not applied to the monitored body part;
$V_C$ is the volume of a known calibrating volume of compressible fluid added to the compressible fluid system after measuring pressure $P_1$;
and $P_2$ is the pressure of the compressible fluid system after said volume $V_C$ of calibrating fluid has been added thereto.

19. The apparatus according to claim 18, wherein said data processor is programmed to determine the volume $V_T$ of the non-compressible tissue according to the following equations:

$$V_F = P_2 \cdot V_C/(P_1 - P_2) \quad \text{(Eq. 2)}$$

$$V_T = V_S - V_F \quad \text{(Eq. 3)}.$$

20. The apparatus according to claim 19, wherein said probe outputs a pulsatile signal corresponding to said sensed arterial volume changes $V_P$, and wherein said data processor is programmed to measure said pressures $P_1$ and $P_2$ at the lowest and highest points $P_{min}$ and $P_{max}$, respectively, of the pulsatile signal outputted by said probe.

21. The apparatus according to claim 20, wherein said data processor is programmed to determine the pulse volumes ($V_P$) according to the following equation:

$$V_P = (P_1 - P_2) \cdot V_{min}/P_2 \quad \text{(Eq. 4)}$$

wherein: $V_{min} = V_T$; and $P_1 = P_{min}$ and $P_2 = P_{max}$.
and said pulse volumes, when multiplied by the fraction $K/V_T$ (K being a constant), thereby serving as an index of pulse size corrected for the tissue volume of the respective patient.

22. The apparatus according to claim 21, wherein the apparatus further comprises temperature and barometric pressure testers, and wherein said data processor is programmed to convert all derived volumes in terms of predetermined standard conditions of atmospheric pressure and temperature.

23. The apparatus according to claim 18, wherein said calibrating means includes:
a pump of known stroke volume for each cycle;
a counter for counting the number of cycles for introducing said compressible fluid into the compressible fluid system at a known rate;
and a data processor for determining the total added volume and the time taken for the pressure in the compressible fluid system to reach a predetermined pressure value.

24. The apparatus according to claim 18, wherein said calibrating means includes:
a pump for introducing said compressible fluid into the compressible fluid system of the probe from a supply of constant (or known) rate of flow of fluid;
means for determining the time interval of flow of the fluid into the compressible fluid system of the probe;

and a data processor for determining the total added volume and the time taken for the pressure in the compressible fluid system to reach a predetermined pressure value.

25. The apparatus according to claim 17, wherein said probe is configured and dimensioned to monitor the peripheral arterial tone of the monitored body part.

26. The apparatus according to claim 25, wherein said calibrating means includes a physical model of a shape similar to that of the body part, and of an adjustable volume which is presettable according to the volume of the body part to receive the probe.

27. The apparatus according to claim 26, wherein said physical model further includes means for effecting predetermined pulsatile volume changes.

28. The apparatus according to claim 26, wherein said physical model includes an outer elastic envelope enclosing a plurality of model sections displaceable relative to each other to change the volume defined by said elastic envelope.

29. The apparatus according to claim 28, wherein said physical model further includes a rotatable cam assembly effective to displace said model sections by the rotation of said cam assembly.

30. The apparatus according to claim 28, wherein said physical model further includes an inflatable bladder effective to displace said model sections by the inflation of said bladder.

31. The apparatus according to claim 26, wherein said physical model includes an inflatable external elastic envelope for adjusting the volume of the model by the inflation of said bladder according to the physical characteristics of the body part of the respective patient.

32. Apparatus for detecting a medical condition of a patient, comprising:
a probe system including a probe to be applied to a measurement site of the patient for sensing volume or volume-related changes in a monitored body part thereat due to pulsatile arterial blood flow in the body part;
and calibrating means for calibrating said probe system for the respective measurement site, according to a predetermined physical characteristic of the body part of the respective patient, and for quantifying the arterial pulse volume thereat;
wherein said probe system includes an optical sensor having a light source and a light receiver;
and wherein said apparatus further includes for calibrating the probe system for the measurement site of the respective patient, a model which modifies said light source to produce in said light receiver a waveform simulating that produced by the pulsatile arterial blood flow in the body part of the respective patient.

33. The apparatus according to claim 32, wherein said model includes a light-transmissive body illuminated by said light source, and a function generator for generating a waveform to drive said light source such as to produce in said light receiver a waveform simulating that produced by the pulsatile arterial blood flow in the body part of the respective patient.

34. The apparatus according to claim 33, wherein said calibrating means includes:
a pump for introducing said compressible fluid into the compressible fluid system of the probe from a calibrated volume generating source;
and a data processor for determining the total added volume and the time taken for the pressure in the compressible fluid system to reach a predetermined pressure value.

35. The apparatus according to claim 34, wherein said calibrated volume generating source, said pressure sensor, and said data processor maintain a constant pressure within said probe system, such that volume changes generated by the said calibrated volume generating source are equal in size but opposite in direction to volume changes in said monitored body part due to pulsatile arterial blood flow in the monitored body part.

36. The apparatus according to claim 32, wherein said model includes:
a porous light-transmissive matrix simulating the vascular bed of the non-compressible tissue in the body part of the respective patient;
a liquid light-absorbing medium;
and a pump for pumping said liquid light-absorbing medium through said porous matrix in a manner analogous to the pulsatile arterial blood flow through the body part of the respective patient.

* * * * *